United States Patent
Kim et al.

(10) Patent No.: US 10,393,747 B2
(45) Date of Patent: Aug. 27, 2019

(54) DIAGNOSTIC METHOD FOR GASTRIC CANCER

(71) Applicant: KOREA ADVANCED INSTITUTE OF SCIENCE AND TECHNOLOGY, Daejeon (KR)

(72) Inventors: Jung Hoe Kim, Daejeon (KR); Sung Hyeon Lee, Seoul (KR); Seung Yeol Park, Hwaseong-si (KR); Jin Man Kim, Daejeon (KR); Hyun Joo An, Daejeon (KR); Jae-Han Kim, Daejeon (KR); Myung Jin Oh, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 226 days.

(21) Appl. No.: 15/113,006

(22) PCT Filed: Oct. 22, 2014

(86) PCT No.: PCT/KR2014/009921
§ 371 (c)(1),
(2) Date: Jul. 20, 2016

(87) PCT Pub. No.: WO2015/126030
PCT Pub. Date: Aug. 27, 2015

(65) Prior Publication Data
US 2016/0356777 A1 Dec. 8, 2016

(30) Foreign Application Priority Data

Feb. 19, 2014 (KR) ........................ 10-2014-0019067

(51) Int. Cl.
*G01N 33/574* (2006.01)
(52) U.S. Cl.
CPC ... *G01N 33/57446* (2013.01); *G01N 2333/00* (2013.01); *G01N 2333/47* (2013.01); *G01N 2400/38* (2013.01)
(58) Field of Classification Search
None
See application file for complete search history.

(56) References Cited

FOREIGN PATENT DOCUMENTS

| JP | 2009-168470 A | 7/2009 |
|----|---------------|--------|
| JP | 5212893 B2 | 6/2013 |
| KR | 10-1130755 B1 | 3/2012 |
| KR | 10-2013-0066481 A | 6/2013 |
| WO | 2013/106886 A1 | 7/2013 |

OTHER PUBLICATIONS

Ohtsubo et al., "Glycosylation in Cellular Mechanisms of Health and Disease", Cell, Sep. 8, 2006, vol. 126, pp. 855-867.
An et al., "Glycomics and disease markers", Current Opinion in Chemical Biology, 2009, vol. 13, pp. 601-607.
Arnold et al., "Evaluation of the serum N-linked glycome for the diagnosis of cancer and chronic inflammation", Proteomics, 2008, vol. 8, pp. 3284-3293.
Apweiler et al., "On the frequency of protein glycosylation, as deduced from analysis of the SWISS-PROT database", Biochimica et Biophysica Acta, 1999, vol. 1473, pp. 4-8.
Siegel et al., "Cancer Statistics, 2013", CA Cancer J Clin., 2013, vol. 63, pp. 11-30.
You et al., "Gastric Dysplasia and Gastric Cancer: Helicobacter pylori, Serum Vitamin C, and Other Risk Factors", Journal of the National Cancer Institute, Oct. 4, 2000, vol. 92, No. 19, pp. 1607-1612.
Saikawa et al., "Gastric carcinogenesis and the cancer stem cell hypothesis", Gastric Cancer, 2010, vol. 13, pp. 11-24.
Bones et al., "Glycomic and Glycoproteomic Analysis of Serum from Patients with Stomach Cancer Reveals Potential Markers Arising from Host Defense Response Mechanisms", J. Proteome Res., 2011, vol. 10, pp. 1246-1265.
Langlois et al., "Biological and clinical significance of haptoglobin polymorphism in humans", Clinical Chemistry, 1996, vol. 42, No. 10, pp. 1589-1600.
Nakano et al., "Site-specific analysis of N-glycans on haptoglobin in sera of patients with pancreatic cancer: A novel approach for the development of tumor markers", Int. J. Cancer, 2008, vol. 122, pp. 2301-2309.
Turner, "HAPTOGLOBIN—A Potential Reporter Molecule for Glycosylation Changes in Disease", Advances in Experimental Medicine and Biology, 1995, vol. 376, pp. 231-238.
Ratanasopa et al., "Trapping of Human Hemoglobin by Haptoglobin: Molecular Mechanisms and Clinical Applications", Antioxidants & Redox Signaling, Nov. 17, 2013, vol. 18, pp. 2364-2374.

(Continued)

*Primary Examiner* — Changhwa J Cheu
(74) *Attorney, Agent, or Firm* — Knobbe Martens Olson & Bear LLP

(57) ABSTRACT

This invention relates to a method for gastric cancer diagnosis through the detection of glycan changes, and to a kit for gastric cancer diagnosis. More specifically, based on the fact that in gastric cancer patient-derived haptoglobin, there are changes in N-linked glycosylation of haptoglobin, which are detected through lectin and mass spectrometery, that is, an increase in fucosylation, increases or significant changes in specific glycan structures depending on the classification of antennary structures, or a remarkable decrease in a high mannose structure of the N-glycan as compared to normal persons, N-glycan structures identified using the changes in N-linked glycosylation of haptoglobin may be usefully used as a diagnosis marker in a method for gastric cancer diagnosis using lectin or mass spectrometry, and a kit for gastric cancer diagnosis.

4 Claims, 4 Drawing Sheets

(56) References Cited

OTHER PUBLICATIONS

Park et al., "N-glycosylation status of β-haptoglobin in sera of patients with colon cancer, chronic inflammatory diseases and normal subjects", International Journal of Cancer, 2010, vol. 126, pp. 142-155.
Park et al., "α1-¾ fucosylation at Asn 241 of β-haptoglobin is a novel marker for colon cancer: a combinatorial approach for development of glycan biomarkers", International Journal of Cancer, 2012, vol. 130, pp. 2366-2376.
Arnold et al., "Novel Glycan Biomarkers for the Detection of Lung Cancer", J. Proteome Res., 2011, vol. 10, pp. 1755-1764.
Tsai et al., "Glycoproteomics analysis to identify a glycoform on haptoglobin associated with lung cancer", Proteomics, 2011, vol. 11, pp. 2162-2170.
Wang, et al., "Ultrasensitive Characterization of Site-Specific Glycosylation of Affinity-Purified Haptoglobin from Lung Cancer Patient Plasma Using 10 μm i.d. Porous Layer Open Tubular Liquid Chromatography-Linear Ion Trap Collision-Induced Dissociation/Electron Transfer Dissociation Mass Spectrometry", Analytical Chemistry, 2011, vol. 83, pp. 2029-2037.
Zhang et al., "N-linked glycan changes of serum haptoglobin β chain in liver disease patients", Molecular BioSystems, 2011, vol. 7, pp. 1621-1628.
Pompach et al., "Site specific Glycoforms of Haptoglobin in Liver Cirrhosis and Hepatocellular Carcinoma", Molecular & Cellular Proteomics, 2013, pp. 1281-1293.
Sanda et al., "Quantitative Liquid Chromatography-Mass Spectrometry-Multiple Reaction Monitoring (LC-MS-MRM) Analysis of Site-specific Glycoforms of Haptoglobin in Liver Disease", Molecular & Cellular Proteomics, 2013, vol. 12, pp. 1294-1305.
Sarrats et al., "Glycosylation of liver acute-phase proteins in pancreatic cancer and chronic pancreatitis", Proteomics Clin. Appl., 2010, vol. 4, pp. 432-448.
Yoon et al., "N-glycosylation status of β-haptoglobin in sera of patients with prostate cancer vs. benign prostate diseases", International Journal of Oncology, 2010, vol. 36, pp. 193-203.
Hirabayashi, "Lectin-based structural glycomics: Glycoproteomics and glycan profiling", Glycoconjugate Journal, 2004, vol. 21, pp. 35-40.
Zhao et al., "Glycoprotein Microarrays with Multi-Lectin Detection: Unique Lectin Binding Patterns as a Tool for Classifying Normal, Chronic Pancreatitis and Pancreatic Cancer Sera", Journal of Proteome Research, 2007, vol. 6, pp. 1864-1874.
Hirabayashi, "Concept, Strategy and Realization of Lectin-based Glycan Profiling", J. Biochem., 2008, vol. 144, pp. 139-147.
Hsu et al., "Sweet tasting chips: microarray-based analysis of glycans", Current Opinion in Chemical Biology, 2009, vol. 13, pp. 427-432.
Chan et al., "Lectin Glycoarray Technologies for Nanoscale Biomedical Detection", Protein & Peptide Letters, 2010 vol. 17, pp. 1417-1425.
Hirabayashi et al., "Lectin-based structural glycomics: A practical approach to complex glycans", Electrophoresis, 2011, vol. 32, pp. 1118-1128.
Dennis et al., "Density-dependent Lectin-Glycan Interactions as a Paradigm for Conditional Regulation by Posttranslational Modifications", Molecular & Cellular Proteomics, 2013, vol. 12, pp. 913-920.
Kletter et al., "Global Comparisons of Lectin-Glycan Interactions Using a Database of Analyzed Glycan Array Data", Mollecular & Cellular Proteomics, 2013, vol. 12, pp. 1026-1035.
He et al., "HPLC analysis of discrete haptoglobin isoform N-linked oligosaccharides following 2D-PAGE isolation", Biochemical and Biophysical Research Communications, 2006, vol. 343, pp. 496-503.
Marino et al., "A systematic approach to protein glycosylation analysis: a path through the maze", Nature Chemical Biology, Oct. 2010, vol. 6, pp. 713-723.
Drake et al., "Sweetening the Pot: Adding Glycosylation to the Biomarker Discovery Equation", Clinical Chemistry, 2010, vol. 56, No. 2, pp. 223-236.
Bones et al., "Ultra Performance Liquid Chromatographic Profiling of Serum N-Glycans for Fast and Efficient Identification of Cancer Associated Alterations in Glycosylation", Analytical Chemistry, 2010, vol. 82, pp. 10208-10215.
Hua et al., "Comprehensive native glycan profiling with isomer separation and quantitation for the discovery of cancer biomarkers", Analyst, 2011, vol. 136, pp. 3663-3671.
Hua et al., "Application of nano-LC-based glycomics towards biomarker discovery", Bioanalysis, 2011, vol. 3, No. 22, pp. 2573-2585.
Hua et al., "Site-specific protein glycosylation analysis with glycan isomer differentiation", Analytical and Bioanalytical Chemistry, 2012, vol. 403, pp. 1291-1302.
Hashii et al., "Glycomic,/glycoproteomic analysis by liquid chromatography/mass spectrometry: Analysis of glycan structural alteration in cells", Proteomics, 2005, vol. 5, pp. 4665-4672.
An et al., "Profiling of Glycans in Serum for the Discovery of Potential Biomarkers for Ovarian Cancer", Journal of Proteome Research, 2006, vol. 5, pp. 1626-1635.
International Search Report dated Jan. 26, 2015 of PCT/KR2014/009921 which is the parent application and its English translation—4 pages.
Chu et al., "Profile of native N-linked glycan structures from human serum using high performance liquid chromatography on a microfluidic chip and time-of-flight mass spectrometry", Proteomics, 2009, vol. 9, pp. 1939-1951.
De Reggi et al., "The glycan moiety of human pancreatic lithostathine—Structure characterization and possible pathophysiological implications", Eur. J. Biochem., 1995, vol. 230, pp. 503-510.
Zhao et al., "Comparative Serum Glycoproteomics Using Lectin Selected Sialic Acid Glycoproteins with Mass Spectrometric Analysis: Application to Pancreatic Cancer Serum", Journal of Proteome Research, 2006, vol. 5, pp. 1792-1802.
Goodarzi et al., "Decreased branching, increased fucosylation and changed sialylation of alpha-1-proteinase inhibitor in breast and ovarian cancer", Clinica Chimica Acta, 1995, vol. 236, pp. 161-171.
Bahk et al., "Antigens secreted from *Mycobacterium tuberculosis*: Identification by proteomics approach and test for diagnostic marker", Proteomics, 2004, vol. 4, pp. 3299-3307.
Zuo et al., "Towards global analysis of mammalian proteomes using sample prefractionation prior to narrow pH range two-dimensional gels and using one-dimensional gels for insoluble and large proteins", Electrophoresis, 2001, vol. 22, pp. 1603-1615.
Oh et al., "Analytical platform for glycomic characterization of recombinant erythropoietin biotherapeutics and biosimilars by MS", Bioanalysis, 2013, vol. 5, No. 5, pp. 545-559.
Clowers et al., "Dual polarity accurate mass calibration for electrospray ionization and matrix-assisted laser desorption/ionization mass spectrometry using maltooligosaccharides", Analytical Biochemistry, 2008, vol. 381, pp. 205-213.
Hua et al., "Isomer-specific chromatographic profiling yields highly sensitive and specific potential N-glycan biomarkers for epithelial ovarian cancer", Journal of Chromatography A, 2013, vol. 1279, pp. 58-67.
Kronewitter et al., "The development of retrosynthetic glycan libraries to profile and classify the human serum N-linked glycome", Proteomics, 2009, vol. 9, pp. 2986-2994.
Hua et al., "Isomer-Specific LC/MS and LC/MS/MS Profiling of the Mouse Serum N-Glycome Revealing a Number of Novel Sialylated N-Glycans", Analytical Chemistry, 2013, vol. 85, pp. 4636-4643.
Bereman et al., "Development of a nanoLC LTQ Orbitrap Mass Spectrometric Method for Profiling Glycans Derived from Plasma from Healthy, Benign Tumor Control, and Epithelial Ovarian Cancer Patients", Analytical Chemistry, 2009, vol. 81, pp. 1130-1136.
Bereman et al., "Development of a Robust and High Throughput Method for Profiling N-Linked Glycans Derived from Plasma Glycoproteins by NanoLC-FTICR Mass Spectrometry", Journal of Proteome Research, 2009, vol. 8, pp. 3764-3770.

(56) References Cited

OTHER PUBLICATIONS

Ninonuevo et al., "Nanoliquid chromatography-mass spectrometry of oligosaccharides employing graphitized carbon chromatography on microchip with a high-accuracy mass analyzer", Electrophoresis, 2005, vol. 26, pp. 3641-3649.

Yin et al., "The fundamental aspects and applications of Agilent HPLC-Chip", J. Sep. Sci., 2007, vol. 30, pp. 1427-1434.

Bynum et al., "Characterization of IgG N-Glycans Employing a Microfluidic Chip that Integrates Glycan Cleavage, Sample Purification, LC Separation, and MS Detection", Analytical Chemistry, 2009, vol. 81, pp. 8818-8825.

Fortier et al., "Integrated Microfluidic Device for Mass Spectrometry-Based Proteomics and Its Application to Biomarker Discovery Programs", Analytical Chemistry, 2005, vol. 77, pp. 1631-1640.

Smith et al., "Application of Microarrays for Deciphering the Structure and Function of the Human Glycome", Mollecular & Cellular Proteomics, 2013, vol. 12, pp. 902-912.

Fujimara et al., "Glycosylation status of haptoglobin in sera of patients with prostate cancer vs. benign prostate disease or normal subjects", Int. J. Cancer, 2008, vol. 122, pp. 39-49.

Mackiewicz et al., "Glycoforms of serum alpha 1-acid glycoprotein as markers of inflammation and cancer", Glycoconjugate Journal, 1995, vol. 12, pp. 241-247.

Yamashita et al., "Altered Glycosylation of Serum Transferrin of Patients with Hepatocellular Carcinoma", Journal of Biological Chemistry, 1989, vol. 264, No. 5, pp. 2415-2423.

Parekh et al., "Association of rheumatoid arthritis and primary osteoarthritis with changes in the glycosylation pattern of total serum IgG", Nature, 1985, vol. 316, pp. 452-457.

Mehta et al., "Increased Levels of Galactose-Deficient Anti-Gal Immunoglobulin G in the Sera of Hepatitis C Virus-Infected Individuals with Fibrosis and Cirrhosis", Journal of Virology, 2008, vol. 82, No. 3, pp. 1259-1270.

Kodar et al., "Immunoglobulin G Fc N-glycan profiling in patients with gastric cancer by LC-ESI-MS: relation to tumor progression and survival", Glycoconjugate Journal, 2012, vol. 29, pp. 57-66.

Park et al., "Dimeric Le(a) (Le(a)-on-Le(a)) status of beta-haptoglobin in sera of colon cancer, chronic inflammatory disease and normal subjects", International Journal of Oncology, 2010, vol. 36, pp. 1291-1297.

Hamid et al., "A strategy to reveal potential glycan markers from serum glycoproteins associated with breast cancer progression", 2008, Glycobiology, 2008, vol. 18, No. 12, pp. 1105-1118.

Saldova et al., "Ovarian cancer is associated with changes in glycosylation in both acute-phase proteins and IgG", Glycobiology, 2007, vol. 17, No. 12, pp. 1344-1356.

Narisada et al., "Identification of an inducible factor secreted by pancreatic cancer cell lines that stimulates the production of fucosylated haptoglobin in hepatoma cells", Biochemical and Biophysical Research Communications, 2008, vol. 377, pp. 792-796.

Kim et al., "Clinical significances of preoperative serum interleukin-6 and C-reactive protein level in operable gastric cancer", BMC Cancer, 2009, vol. 9, No. 155, pp. 1471-2407.

Comunale et al., "Linkage Specific Fucosylation of Alpha-1-Antitrypsin in Liver Cirrhosis and Cancer Patients: Implications for a Biomarker of Hepatocellular Carcinoma", PLoS One, 2010, vol. 5, No. 8, e12419.

Taketa et al., "A Collaborative Study for the Evaluation of Lectin-Reactive Alpha-Fetoproteins in Early Detection of Hepatocellular Carcinoma", Cancer Research, 1993, vol. 53, pp. 5419-5423.

Wuhrer et al., "Mass spectrometry of proton adducts of fucosylated N-glycans: fucose transfer between antennae gives rise to misleading fragments", Rapid Communication in Mass Spectrometry, 2006, vol. 20, pp. 1747-1754.

Abbott et al., "Targeted Glycoproteomic Identification of Biomarkers for Human Breast Carcinoma", Journal of Proteome Research, 2008, vol. 7, pp. 1470-1480.

Hakomori, "Glycosylation defining cancer malignancy: New wine in an old bottle", Proc. Natl. Acad. Sci. USA, 2002, vol. 99, No. 16, pp. 10231-10233.

Huang et al., "Downregulation of the GnT-V gene inhibits metastasis and invasion of BGC823 gastric cancer cells", Oncology Reports, 2013, vol. 29, pp. 2392-2400.

De Leoz et al., "High-Mannose Glycans are Elevated During Breast Cancer Progression", Molecular & Cellular Proteomics, 2011, vol. 10, M110.002717.

Kyselova et al., "Alterations in the Serum Glycome Due to Metastatic Prostate Cancer", Journal of Proteome Research, 2007, vol. 6, pp. 1822-1832.

DIAGNOSTIC METHOD FOR GASTRIC CANCER

TECHNICAL FIELD

The present invention relates, in general, to a method for gastric cancer diagnosis through the detection of glycan changes, a kit for gastric cancer diagnosis, and a method for detecting glycan changes in order to provide gastric cancer diagnosis information. More particularly, the present invention relates, in general, to a method for gastric cancer diagnosis using N-glycan changes of blood-derived haptoglobin detected through lectin and mass spectrometry, and a kit for gastric cancer diagnosis.

BACKGROUND ART

In general, cancer is the most common cause of death in the world, and this situation is similar in Korea. Cancer is caused and aggravated by genetic or environmental factors, and incidences of cancer and cancer deaths are on the rise due to changes in diet, increases in environmental contamination, increases in exposure to environmental and mental stress, and the like. As compared to other diseases, a feature of cancer is that it is relatively difficult to completely cure, and on average the survival rate after treatment is low. A feature of cancer associated with the survival rate is that there are large differences in prognosis and the survival rate depending on the progress stage of cancer. In spite of 100 years of the development of technologies for treating cancer, complete cure rates of late-stage cancer or metastatic cancer patients are significantly low (Etzioni R. et al., Nature Reviews Cancer 3, 243-252, 2003). Further, generally, there are no subjective symptoms in early stage of cancer, and in the cases in which cancer is diagnosed by subjective symptoms, frequently, cancer is already at a late stage when it is incurable. That is, in order to effectively treat cancer and increase a survival rate, there is a need to develop a method capable of diagnosing cancer at an early stage when it is curable, in addition to a method for treating cancer. To this end, research into the development of a biofactor, that is, a biomarker capable of assisting in early diagnosis of cancer, is currently actively being conducted around the world based on proteomics.

A tumor biomarker may be variously used. For example, the cancer biomarker may assist in early diagnosis of cancer and enable measurement of a progression stage of cancer, monitoring of a progression state of cancer depending on treatment, and determination of prognosis after operation (Rifai N. et al., Nature Biotech., 24, 971-983, 2006). In order to detect cancer and trace the progression state of cancer using the biomarker having the above-mentioned purposes and functions, a non-destructive method is required. Therefore, body fluids such as blood, and the like, of which examination is not dangerous, are recognized as optimal biosamples for developing the biomarker. That is, the most standardized approach for develop a cancer biomarker is to develop a biomarker capable of detecting cancer using urine, saliva, blood, or the like. Among them, blood may be the most comprehensive biosample in which proteins derived from all tissues are concentrated. Further, in view of a form of a bio material, the most preferable form of the tumor biomarker may be a protein.

Among methods for diagnosing a patient with gastric cancer, which is of the most common cancer in Korea, the most frequently used examination methods are gastroscopy, ultrasound test, and the like. However, since in these methods for gastric cancer diagnosis, expensive medical equipment is used, diagnosis costs too much, and some patients may be reluctant to undergo gastroscopy.

Due to these problems, there is a need to develop a tumor biomarker applicable to an in vitro diagnosis technology capable of detecting cancer using a small amount of body fluid, particularly, blood. At present, actually, there is no FDA approved blood-derived biomarker associated with gastric cancer.

In view that 50% or more of proteins in the body are glycoproteins, various human diseases are more likely to be associated with the glycoproteins. Therefore, it is possible to develop a diagnosis marker by screening glycoproteins associated with diseases, and analyzing disease-specific glycan structures thereof.

Most of the biochemical studies on cancer are focused on protein expression changes, but, in accordance with the development of a technology of analyzing glycan structures, glucoconjugates have become increasingly important. It is known that tumor development may be labeled with glycosylation, which is one of post-translational modification processes, but until now, accurate scientific reasons why a glycan structure is changed in tumor has not been found yet. However, these cancer-specific glycans may be released to the blood, and these glycans may be used for diagnosis by using various kinds of antibodies, and the like.

Lectins derived from plants may recognize various glycan structures. Since these lectins may be easily used, and are cheap, the lectins have been mainly used to detect glycan structures. Further, recently, methods capable of analyzing a tracer amount of glycan using an advanced mass spectrometer have been developed.

RELATED ART DOCUMENT

Non-Patent Document (Non-Patent Document 1) Ohtsubo, K., and Marth, J. D. (2006) Glycosylation in cellular mechanisms of health and disease. Cell 126, 855-867

(Non-Patent Document 2) An, H. J., Kronewitter, S. R., de Leoz, M. L., and Lebrilla, C. B. (2009) Glycomics and disease markers. Curr Opin Chem Biol 13, 601-607

(Non-Patent Document 3) Arnold, J. N., Saldova, R., Hamid, U. M., and Rudd, P. M. (2008) Evaluation of the serum N-linked glycome for the diagnosis of cancer and chronic inflammation. Proteomics 8, 3284-3293

(Non-Patent Document 4) Apweiler, R., Hermjakob, H., and Sharon, N. (1999) On the frequency of protein glycosylation, as deduced from analysis of the SWISS-PROT database. Biochim Biophys Acta 1473, 4-8

(Non-Patent Document 5) Siegel, R., Naishadham, D., and Jemal, A. (2013) Cancer statistics, 2013. CA Cancer J Clin 63, 11-30

(Non-Patent Document 6) You, W. C., Zhang, L., Gail, M. H., Chang, Y. S., Liu, W. D., Ma, J. L., Li, J. Y., Jin, M. L., Hu, Y. R., Yang, C. S., Blaser, M. J., Correa, P., Blot, W. J., Fraumeni, J. F., and Xu, G. W. (2000) Gastric dysplasia and gastric cancer: *Helicobacter pylori*, serum vitamin C, and other risk factors. J Natl Cancer Inst 92, 1607-1612

(Non-Patent Document 7) Saikawa, Y., Fukuda, K., Takahashi, T., Nakamura, R., Takeuchi, H., and Kitagawa, Y. (2010) Gastric carcinogenesis and the cancer stem cell hypothesis. Gastric Cancer 13, 11-24

(Non-Patent Document 8) Bones, J., Byrne, J. C., O'Donoghue, N., McManus, C., Scaife, C., Boissin, H., Nastase, A., and Rudd, P. M. (2011) Glycomic and glycoproteomic analysis of serum from patients with stomach cancer reveals potential markers arising from host defense response mechanisms. J Proteome Res 10, 1246-1265

(Non-Patent Document 9) Langlois, M. R., and Delanghe, J. R. (1996) Biological and clinical significance of haptoglobin polymorphism in humans. Clin Chem 42, 1589-1600

(Non-Patent Document 10) Nakano, M., Nakagawa, T., I to, T., Kitada, T., Hijioka, T., Kasahara, A., Tajiri, M., Wada, Y., Taniguchi, N., and Miyoshi, E. (2008) Site-specific analysis of N-glycans on haptoglobin in sera of patients with pancreatic cancer: a novel approach for the development of tumor markers. Int J Cancer 122, 2301-2309

(Non-Patent Document 11) Turner, G. A. (1995) Haptoglobin. A potential reporter molecule for glycosylation changes in disease. Adv Exp Med Biol 376, 231-238

(Non-Patent Document 12) Ratanasopa, K., Chakane, S., Ilyas, M., Nantasenamat, C., and Bulow, L. (2013) Trapping of human hemoglobin by haptoglobin: molecular mechanisms and clinical applications. Antioxid Redox Signal 18, 2364-2374

(Non-Patent Document 13) Park, S. Y., Yoon, S. J., Jeong, Y. T., Kim, J. M., Kim, J. Y., Bernert, B., Ullman, T., Itzkowitz, S. H., Kim, J. H., and Hakomori, S. I. (2010) N-glycosylation status of beta-haptoglobin in sera of patients with colon cancer, chronic inflammatory diseases and normal subjects. Int J Cancer 126, 142-155

(Non-Patent Document 14) Park, S. Y., Lee, S. H., Kawasaki, N., Itoh, S., Kang, K., Hee Ryu, S., Hashii, N., Kim, J. M., Kim, J. Y., and Hoe Kim, J. (2012) α1-3/4 fucosylation at Asn 241 of β-haptoglobin is a novel marker for colon cancer: a combinatorial approach for development of glycan biomarkers. Int J Cancer 130, 2366-2376

(Non-Patent Document 15) Arnold, J. N., Saldova, R., Galligan, M. C., Murphy, T. B., Mimura-Kimura, Y., Telford, J. E., Godwin, A. K., and Rudd, P. M. (2011) Novel glycan biomarkers for the detection of lung cancer. J Proteome Res 10, 1755-1764

(Non-Patent Document 16) Tsai, H. Y., Boonyapranai, K., Sriyam, S., Yu, C. J., Wu, S. W., Khoo, K. H., Phutrakul, S., and Chen, S. T. (2011) Glycoproteomics analysis to identify a glycoform on haptoglobin associated with lung cancer. Proteomics 11, 2162-2170

(Non-Patent Document 17) Wang, D., Hincapie, M., Rejtar, T., and Karger, B. L. (2011) Ultrasensitive characterization of site-specific glycosylation of affinity-purified haptoglobin from lung cancer patient plasma using 10 μm i.d. porous layer open tubular liquid chromatography-linear ion trap collision-induced dissociation/electron transfer dissociation mass spectrometry. Anal Chem 83, 2029-2037

(Non-Patent Document 18) Zhang, S., Shu, H., Luo, K., Kang, X., Zhang, Y., Lu, H., and Liu, Y. (2011) N-linked glycan changes of serum haptoglobin β chain in liver disease patients. Mol Biosyst 7, 1621-1628

(Non-Patent Document 19) Pompach, P., Brnakova, Z., Sanda, M., Wu, J., Edwards, N., and Goldman, R. (2013) Site specific glycoforms of haptoglobin in liver cirrhosis and hepatocellular carcinoma. Mol Cell Proteomics (Non-Patent Document 20) Sanda, M., Pompach, P., Brnakova, Z., Wu, J., Makambi, K., and Goldman, R. (2013) Quantitative liquid chromatography-mass spectrometry-multiple reaction monitoring (LC-MS-MRM) analysis of site-specific glycoforms of haptoglobin in liver disease. Mol Cell Proteomics 12, 1294-1305

(Non-Patent Document 21) Sarrats, A., Saldova, R., Pla, E., Fort, E., Harvey, D. J., Struwe, W. B., de Llorens, R., Rudd, P. M., and Peracaula, R. (2010) Glycosylation of liver acute-phase proteins in pancreatic cancer and chronic pancreatitis. Proteomics Clin Appl 4, 432-448

(Non-Patent Document 22) Yoon, S. J., Park, S. Y., Pang, P. C., Gallagher, J., Gottesman, J. E., Dell, A., Kim, J. H., and Hakomori, S. I. (2010) N-glycosylation status of beta-haptoglobin in sera of patients with prostate cancer vs. benign prostate diseases. Int J Oncol 36, 193-203

(Non-Patent Document 23) Hirabayashi, J. (2004) Lectin-based structural glycomics: glycoproteomics and glycan profiling. Glycoconj J 21, 35-40

(Non-Patent Document 24) Zhao, J., Patwa, T. H., Qiu, W., Shedden, K., Hinderer, R., Misek, D. E., Anderson, M. A., Simeone, D. M., and Lubman, D. M. (2007) Glycoprotein microarrays with multi-lectin detection: unique lectin binding patterns as a tool for classifying normal, chronic pancreatitis and pancreatic cancer sera. J Proteome Res 6, 1864-1874

(Non-Patent Document 25) Hirabayashi, J. (2008) Concept, strategy and realization of lectin-based glycan profiling. J Biochem 144, 139-147

(Non-Patent Document 26) Hsu, K. L., and Mahal, L. K. (2009) Sweet tasting chips: microarray-based analysis of glycans. Curr Opin Chem Biol 13, 427-432

(Non-Patent Document 27) Chan, K., and Ng, T. B. (2010) Lectin glycoarrays technologies for nanoscale biomedical detection. Protein Pept Lett 17, 1417-1425

(Non-Patent Document 28) Hirabayashi, J., Kuno, A., and Tateno, H. (2011) Lectin-based structural glycomics: a practical approach to complex glycans. Electrophoresis 32, 1118-1128

(Non-Patent Document 29) Dennis, J. W., and Brewer, C. F. (2013) Density-dependent lectin-glycan interactions as a paradigm for conditional regulation by posttranslational modifications. Mol Cell Proteomics 12, 913-920

(Non-Patent Document 30) Kletter, D., Singh, S., Bern, M., and Haab, B. B. (2013) Global comparisons of lectin-glycan interactions using a database of analyzed glycan array data. Mol Cell Proteomics 12, 1026-1035

(Non-Patent Document 31) He, Z., Aristoteli, L. P., Kritharides, L., and Garner, B. (2006) HPLC analysis of discrete haptoglobin isoform N-linked oligosaccharides following 2D-PAGE isolation. Biochem Biophys Res Commun 343, 496-503

(Non-Patent Document 32) Marino, K., Bones, J., Kattla, J. J., and Rudd, P. M. (2010) A systematic approach to protein glycosylation analysis: a path through the maze. Nat Chem Biol 6, 713-723

(Non-Patent Document 33) Drake, P. M., Cho, W., Li, B., Prakobphol, A., Johansen, E., Anderson, N. L., Regnier, F. E., Gibson, B. W., and Fisher, S. J. (2010) Sweetening the pot: adding glycosylation to the biomarker discovery equation. Clin Chem 56, 223-236

(Non-Patent Document 34) Bones, J., Mittermayr, S., O'Donoghue, N., Guttman, A., and Rudd, P. M. (2010) Ultra performance liquid chromatographic profiling of serum N-glycans for fast and efficient identification of cancer associated alterations in glycosylation. Anal Chem 82, 10208-10215

(Non-Patent Document 35) Hua, S., An, H. J., Ozcan, S., Ro, G. S., Soares, S., DeVere-White, R., and Lebrilla, C. B. (2011) Comprehensive native glycan profiling with isomer separation and quantitation for the discovery of cancer biomarkers. Analyst 136, 3663-3671

(Non-Patent Document 36) Hua, S., Lebrilla, C., and An, H. J. (2011) Application of nano-LC-based glycomics towards biomarker discovery. Bioanalysis 3, 2573-2585

(Non-Patent Document 37) Hua, S., Nwosu, C. C., Strum, J. S., Seipert, R. R., An, H. J., Zivkovic, A. M., German, J. B., and Lebrilla, C. B. (2012) Site-specific protein glycosylation analysis with glycan isomer differentiation. Anal Bioanal Chem 403, 1291-1302

(Non-Patent Document 38) Hashii, N., Kawasaki, N., Itoh, S., Hyuga, M., Kawanishi, T., and Hayakawa, T. (2005) Glycomic/glycoproteomic analysis by liquid chromatography/mass spectrometry: analysis of glycan structural alteration in cells. Proteomics 5, 4665-4672

(Non-Patent Document 39) An, H. J., Miyamoto, S., Lancaster, K. S., Kirmiz, C., Li, B., Lam, K. S., Leiserowitz, G. S., and Lebrilla, C. B. (2006) Profiling of glycans in serum for the discovery of potential biomarkers for ovarian cancer. J Proteome Res 5, 1626-1635

(Non-Patent Document 40) Chu, C. S., Ninonuevo, M. R., Clowers, B. H., Perkins, P. D., An, H. J., Yin, H., Killeen, K., Miyamoto, S., Grimm, R., and Lebrilla, C. B. (2009) Profile of native N-linked glycan structures from human serum using high performance liquid chromatography on a microfluidic chip and time-of-flight mass spectrometry. Proteomics 9, 1939-1951

(Non-Patent Document 41) De Reggi, M., Capon, C., Gharib, B., Wieruszeski, J. M., Michel, R., and Fournet, B. (1995) The glycan moiety of human pancreatic lithostathine. Structure characterization and possible pathophysiological implications. Eur J Biochem 230, 503-510

(Non-Patent Document 42) Zhao, J., Simeone, D. M., Heidt, D., Anderson, M. A., and Lubman, D. M. (2006) Comparative serum glycoproteomics using lectin selected sialic acid glycoproteins with mass spectrometric analysis: application to pancreatic cancer serum. J Proteome Res 5, 1792-1802

(Non-Patent Document 43) Goodarzi, M. T., and Turner, G. A. (1995) Decreased branching, increased fucosylation and changed sialylation of alpha-1-proteinase inhibitor in breast and ovarian cancer. Clin Chim Acta 236, 161-171

(Non-Patent Document 44) Bahk, Y. Y., Kim, S. A., Kim, J. S., Euh, H. J., Bai, G. H., Cho, S. N., and Kim, Y. S. (2004) Antigens secreted from *Mycobacterium tuberculosis*: identification by proteomics approach and test for diagnostic marker. Proteomics 4, 3299-3307

(Non-Patent Document 45) Zuo, X., Echan, L., Hembach, P., Tang, H. Y., Speicher, K. D., Santoli, D., and Speicher, D. W. (2001) Towards global analysis of mammalian proteomes using sample prefractionation prior to narrow pH range two-dimensional gels and using one-dimensional gels for insoluble and large proteins. Electrophoresis 22, 1603-1615

(Non-Patent Document 46) Oh, M. J., Hua, S., Kim, B. J., Jeong, H. N., Jeong, S. H., Grimm, R., Yoo, J. S., and An, H. J. (2013) Analytical platform for glycomic characterization of recombinant erythropoietin biotherapeutics and biosimilars by MS. Bioanalysis 5, 545-559

(Non-Patent Document 47) Clowers, B. H., Dodds, E. D., Seipert, R. R., and Lebrilla, C. B. (2008) Dual polarity accurate mass calibration for electrospray ionization and matrix-assisted laser desorption/ionization mass spectrometry using maltooligosaccharides. Analytical Biochemistry 381, 205-213

(Non-Patent Document 48) Hua, S., Williams, C. C., Dimapasoc, L. M., Ro, G. S., Ozcan, S., Miyamoto, S., Lebrilla, C. B., An, H. J., and Leiserowitz, G. S. (2013) Isomer-specific chromatographic profiling yields highly sensitive and specific potential N-glycan biomarkers for epithelial ovarian cancer. Journal of Chromatography A 1279, 58-67

(Non-Patent Document 49) Hua, S., Nwosu, C., Strum, J., Seipert, R., An, H., Zivkovic, A., German, J., and Lebrilla, C. (2012) Site-specific protein glycosylation analysis with glycan isomer differentiation. Anal Bioanal Chem 403, 1291-1302

(Non-Patent Document 50) Kronewitter, S. R., An, H. J., de Leoz, M. L., Lebrilla, C. B., Miyamoto, S., and Leiserowitz, G. S. (2009) The development of retrosynthetic glycan libraries to profile and classify the human serum N-linked glycome. Proteomics 9, 2986-2994

(Non-Patent Document 51) Hua, S., Jeong, H. N., Dimapasoc, L. M., Kang, I., Han, C., Choi, J. S., Lebrilla, C. B., and An, H. J. (2013) Isomer-Specific LC/MS and LC/MS/MS Profiling of the Mouse Serum N-Glycome Revealing a Number of Novel Sialylated N-Glycans. Anal Chem (Non-Patent Document 52) Bereman, M. S., Williams, T. I., and Muddiman, D. C. (2009) Development of a nanoLC LTQ orbitrap mass spectrometric method for profiling glycans derived from plasma from healthy, benign tumor control, and epithelial ovarian cancer patients. Anal Chem 81, 1130-1136

(Non-Patent Document 53) Bereman, M. S., Young, D. D., Deiters, A., and Muddiman, D. C. (2009) Development of a robust and high throughput method for profiling N-linked glycans derived from plasma glycoproteins by NanoLC-FTICR mass spectrometry. J Proteome Res 8, 3764-3770

(Non-Patent Document 54) Ninonuevo, M., An, H., Yin, H., Killeen, K., Grimm, R., Ward, R., German, B., and Lebrilla, C. (2005) Nanoliquid chromatography-mass spectrometry of oligosaccharides employing graphitized carbon chromatography on microchip with a high-accuracy mass analyzer. Electrophoresis 26, 3641-3649

(Non-Patent Document 55) Yin, H., and Killeen, K. (2007) The fundamental aspects and applications of Agilent HPLC-Chip. J Sep Sci 30, 1427-1434

(Non-Patent Document 56) Bynum, M. A., Yin, H., Felts, K., Lee, Y. M., Monell, C. R., and Killeen, K. (2009) Characterization of IgG N-glycans employing a microfluidic chip that integrates glycan cleavage, sample purification, LC separation, and MS detection. Anal Chem 81, 8818-8825

(Non-Patent Document 57) Fortier, M. H., Bonneil, E., Goodley, P., and Thibault, P. (2005) Integrated microfluidic device for mass spectrometry-based proteomics and its application to biomarker discovery programs. Anal Chem 77, 1631-1640

(Non-Patent Document 58) Smith, D. F., and Cummings, R. D. (2013) Application of microarrays for deciphering the structure and function of the human glycome. Mol Cell Proteomics 12, 902-912

(Non-Patent Document 59) Fujimura, T., Shinohara, Y., Tissot, B., Pang, P. C., Kurogochi, M., Saito, S., Arai, Y., Sadilek, M., Murayama, K., Dell, A., Nishimura, S., and Hakomori, S. I. (2008) Glycosylation status of haptoglobin in sera of patients with prostate cancer vs. benign prostate disease or normal subjects. Int J Cancer 122, 39-49

(Non-Patent Document 60) Mackiewicz, A., and Mackiewicz, K. (1995) Glycoforms of serum alpha 1-acid glycoprotein as markers of inflammation and cancer. Glycoconj J 12, 241-247

(Non-Patent Document 61) Yamashita, K., Koide, N., Endo, T., Iwaki, Y., and Kobata, A. (1989) Altered glycosylation of serum transferrin of patients with hepatocellular carcinoma. J Biol Chem 264, 2415-2423

(Non-Patent Document 62) Parekh, R. B., Dwek, R. A., Sutton, B. J., Fernandes, D. L., Leung, A., Stanworth, D., Rademacher, T. W., Mizuochi, T., Taniguchi, T., and Matsuta, K. (1985) Association of rheumatoid arthritis and primary osteoarthritis with changes in the glycosylation pattern of total serum IgG. Nature 316, 452-457

(Non-Patent Document 63) Mehta, A. S., Long, R. E., Comunale, M. A., Wang, M., Rodemich, L., Krakover, J., Philip, R., Marrero, J. A., Dwek, R. A., and Block, T. M. (2008) Increased levels of galactose-deficient anti-Gal immunoglobulin G in the sera of hepatitis C virus-infected individuals with fibrosis and cirrhosis. J Virol 82, 1259-1270

(Non-Patent Document 64) Kodar, K., Stadlmann, J., Klaamas, K., Sergeyev, B., and Kurtenkov, O. (2012) Immunoglobulin G Fc N-glycan profiling in patients with gastric cancer by LC-ESI-MS: relation to tumor progression and survival. Glycoconj J 29, 57-66

(Non-Patent Document 65) Park, S. Y., Yoon, S. J., Hakomori, S. I., Kim, J. M., Kim, J. Y., Bernert, B., Ullman, T., Itzkowitz, S. H., and Kim, J. H. (2010) Dimeric Le(a) (Le(a)-on-Le(a)) status of beta-haptoglobin in sera of colon cancer, chronic inflammatory disease and normal subjects. Int J Oncol 36, 1291-1297

(Non-Patent Document 66) Abd Hamid, U. M., Royle, L., Saldova, R., Radcliffe, C. M., Harvey, D. J., Storr, S. J., Pardo, M., Antrobus, R., Chapman, C. J., Zitzmann, N., Robertson, J. F., Dwek, R. A., and Rudd, P. M. (2008) A strategy to reveal potential glycan markers from serum glycoproteins associated with breast cancer progression. Glycobiology 18, 1105-1118

(Non-Patent Document 67) Saldova, R., Royle, L., Radcliffe, C. M., Abd Hamid, U. M., Evans, R., Arnold, J. N., Banks, R. E., Hutson, R., Harvey, D. J., Antrobus, R., Petrescu, S. M., Dwek, R. A., and Rudd, P. M. (2007) Ovarian cancer is associated with changes in glycosylation in both acute-phase proteins and IgG. Glycobiology 17, 1344-1356

(Non-Patent Document 68) Narisada, M., Kawamoto, S., Kuwamoto, K., Moriwaki, K., Nakagawa, T., Matsumoto, H., Asahi, M., Koyama, N., and Miyoshi, E. (2008) Identification of an inducible factor secreted by pancreatic cancer cell lines that stimulates the production of fucosylated haptoglobin in hepatoma cells. Biochem Biophys Res Commun 377, 792-796

(Non-Patent Document 69) Kim, D. K., Oh, S. Y., Kwon, H. C., Lee, S., Kwon, K. A., Kim, B. G., Kim, S. G., Kim, S. H., Jang, J. S., Kim, M. C., Kim, K. H., Han, J. Y., and Kim, H. J. (2009) Clinical significances of preoperative serum interleukin-6 and C-reactive protein level in operable gastric cancer. BMC Cancer 9, 155

(Non-Patent Document 70) Comunale, M. A., Rodemich-Betesh, L., Hafner, J., Wang, M., Norton, P., Di Bisceglie, A. M., Block, T., and Mehta, A. (2010) Linkage specific fucosylation of alpha-1-antitrypsin in liver cirrhosis and cancer patients: implications for a biomarker of hepatocellular carcinoma. PLoS One 5, e12419

(Non-Patent Document 71) Taketa, K., Endo, Y., Sekiya, C., Tanikawa, K., Koji, T., Taga, H., Satomura, S., Matsuura, S., Kawai, T., and Hirai, H. (1993) A collaborative study for the evaluation of lectin-reactive alpha-fetoproteins in early detection of hepatocellular carcinoma. Cancer Res 53, 5419-5423

(Non-Patent Document 72) Wuhrer, M., Koeleman, C. A., Hokke, C. H., and Deelder, A. M. (2006) Mass spectrometry of proton adducts of fucosylated N-glycans: fucose transfer between antennae gives rise to misleading fragments. Rapid Commun Mass Spectrom 20, 1747-1754

(Non-Patent Document 73) Abbott, K. L., Aoki, K., Lim, J. M., Porterfield, M., Johnson, R., O'Regan, R. M., Wells, L., Tiemeyer, M., and Pierce, M. (2008) Targeted glycoproteomic identification of biomarkers for human breast carcinoma. J Proteome Res 7, 1470-1480

(Non-Patent Document 74) Hakomori, S. (2002) Glycosylation defining cancer malignancy: new wine in an old bottle. Proc Natl Acad Sci USA 99, 10231-10233

(Non-Patent Document 75) Huang, B., Sun, L., Cao, J., Zhang, Y., Wu, Q., Zhang, J., Ge, Y., Fu, L., and Wang, Z. (2013) Downregulation of the GnT-V gene inhibits metastasis and invasion of BGC823 gastric cancer cells. Oncol Rep 29, 2392-2400

(Non-Patent Document 76) de Leoz, M. L., Young, L. J., An, H. J., Kronewitter, S. R., Kim, J., Miyamoto, S., Borowsky, A. D., Chew, H. K., and Lebrilla, C. B. (2011) High-mannose glycans are elevated during breast cancer progression. Mol Cell Proteomics 10, M110.002717

(Non-Patent Document 77) Kyselova, Z., Mechref, Y., Al Bataineh, M. M., Dobrolecki, L. E., Hickey, R. J., Vinson, J., Sweeney, C. J., and Novotny, M. V. (2007) Alterations in the serum glycome due to metastatic prostate cancer. J Proteome Res 6, 1822-1832

DISCLOSURE

Technical Problem

Accordingly, the present invention has been made keeping in mind the above problems occurring in the related art, and the present invention is intended to propose an excellent biomarker for gastric cancer diagnosis.

Further, the present invention is intended to propose a kit for gastric cancer diagnosis.

In addition, the present invention is intended to propose a method for analyzing a gastric cancer biomarker for rapid and sensitive gastric cancer diagnosis.

Technical Solution

The present inventors sensed gastric cancer-specific glycan changes in glycoproteins in blood using lectin, identified haptoglobin, a glycoprotein corresponding thereto, and purified the identified haptoglobin, thereby confirming a gastric cancer-specific glycan different from that in a normal person by using lectin and a mass spectrometer. The present inventors performed lectin blotting on haptoglobin by using lectin, and quantitative and qualitative information of a N-glycan obtained by treating haptoglobin with PNGase F and a position of fucose in a glycan structure were confirmed using the mass spectrometer.

Advantageous Effects

According to the present invention having the above-described characteristics, it is possible to provide a method for gastric cancer diagnosis based on *Aleuria aurantia* agglutinin (AAL) lectin and *Phaseolus vulgaris*-L agglutinin (PHA-L) lectin having reactivity to a glycan structure by observing that fucosylatin or 1-6 GlcNAc branching in haptoglobin derived from serum of the gastric cancer patient group was remarkably increased as compared to the normal control group.

In addition, according to the present invention having the above-described characteristics, it is possible to provide a method capable of confirming a plurality of high-sensitivity and high-specificity glycan structures, of which abundances are remarkably different in haptoglobin derived from the gastric cancer patient group as compared to the normal control group, at once through mass spectrometry of glycans according to the present invention, and capable of diagnosing gastric cancer using the glycan structures unlike a method according to the related art for analyzing only an amount of a specific protein.

DESCRIPTION OF DRAWINGS

FIG. 3A illustrates overlay chromatogram of an isomer of a tri-antennary structure, Hex6-HexNAc5-Fuc1 (6510, m/z 2151.774), and FIG. 3B illustrates a collision-induced dissociation (CID) spectrum of an isoform of a tri-antennary glycan structure having an outer arm fucose derived from serum of a gastric cancer patient.

EMBODIMENTS

Figures 1A, 1B:
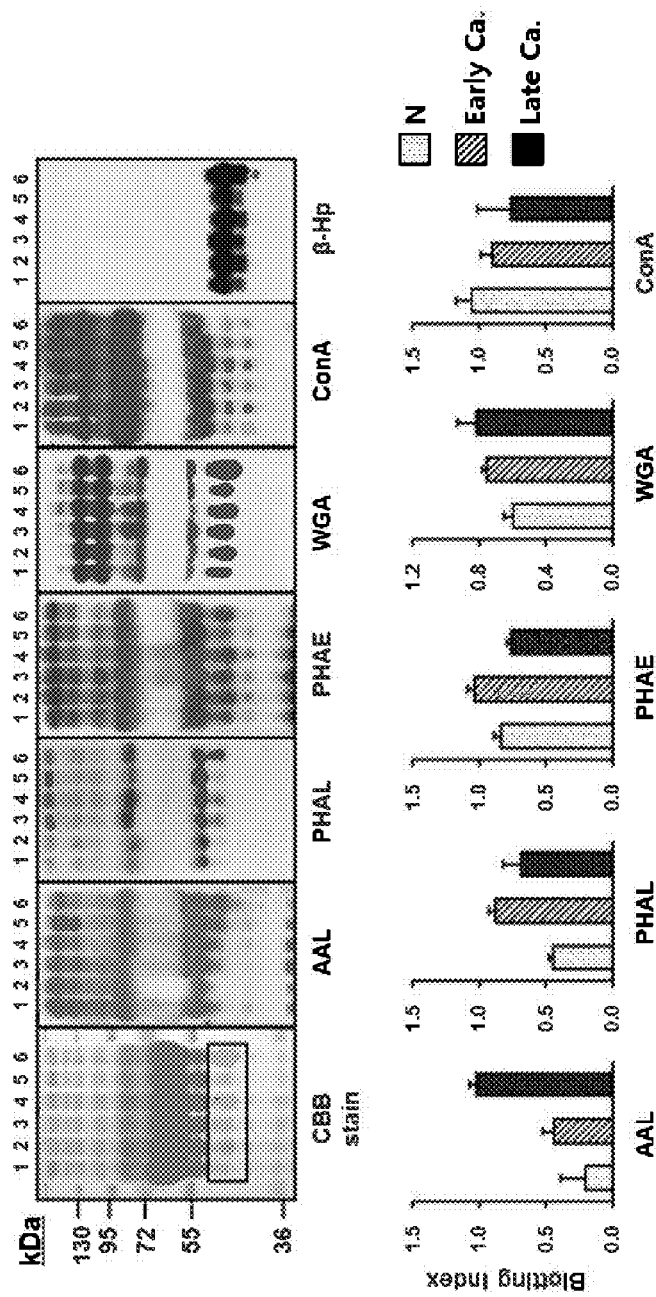
FIGS. 1A and 1B illustrate results obtained by screening glycan patterns present in serum of normal persons and gastric cancer patients using various lectins. Lines 1-2 show normal serum; lines 3-4 show stage I gastric cancer, and stage II gastric cancer; and lines 5-6 show stage III gastric cancer, and stage IV gastric cancer. A blotting index indicates a value obtained by dividing a band intensity in lectin blotting by a band intensity in western blotting.

Reference will now be made in greater detail to an embodiment of the present invention, an example of which is illustrated in the accompanying drawings. Wherever possible, the same reference numerals will be used throughout the drawings and the description to refer to the same or like parts.

The present inventors observed significant increases in specific fucosylation and a high antennary structure in haptoglobins of a late-stage gastric cancer patient as well as an early-stage gastric cancer patient, as compared to a normal control group. Improper glycosylation of haptoglobin of a gastric cancer patient was probed by various combinations of glycomics analysis such as lectin blotting after immunoaffinity purification of a serum-derived haptoglobin, matrix assisted laser desorption/Ionization-time of flight (MALDI-TOF) mass spectrometry (MS), chip-based nano-LC/TOF-MS (LC/MS), and targeted MS/MS by collision-induced dissociation (CID) fragmentation.

A result of the present invention clearly shows that AAL lectin and PHA-L lectin blotting was high in serum haptoglobin of the gastric cancer patient as compared to the normal control group (FIGS. 1A and 1B). In order to confirm a protein having an improper glycan in crude serum, the present inventors performed glycoproteomics in which methods such as sodium dodecyl sulfate-polyacrylamide gel electrophoresis (SDS-PAGE), various lectin blottings, and confirmation of spots sensitive to a target lectin using LC-MS/MS are combined with each other, thereby observing that there was a difference in lectin binding between the normal control group and the gastric cancer patient in a glycoprotein spot having a molecular weight of about 45 kDa. Since lectins may be commercially obtained in the field of glycomics and easily applied to experiments, lectins are widely used to confirm glycan structures associated with specific glycosylation pathways. Interestingly, in the serum of the gastric cancer patient group, increases in fucosylation and high antennary structure of this spot were observed as compared to the normal control group. As a result of LC-MS/MS analysis after in-gel trypsin digestion, this spot was identified as haptoglobin, and a molecular weight thereof was confirmed by anti-haptoglobin western blotting. Haptoglobin is one of the abundant glycoproteins and is a main acute phase protein increased in progression stages of various diseases such as inflammation, tumors, and the like. It is known that haptoglobin has four N-glycosylation sites at asparagines residues 184, 207, 211, and 241, and a single O-glycosylation site. However, it is not known what type of glycosylation and what glycosylation site provide glycan changes distinguished between the gastric cancer patient and the normal control group.

Figures 4A, 4B:
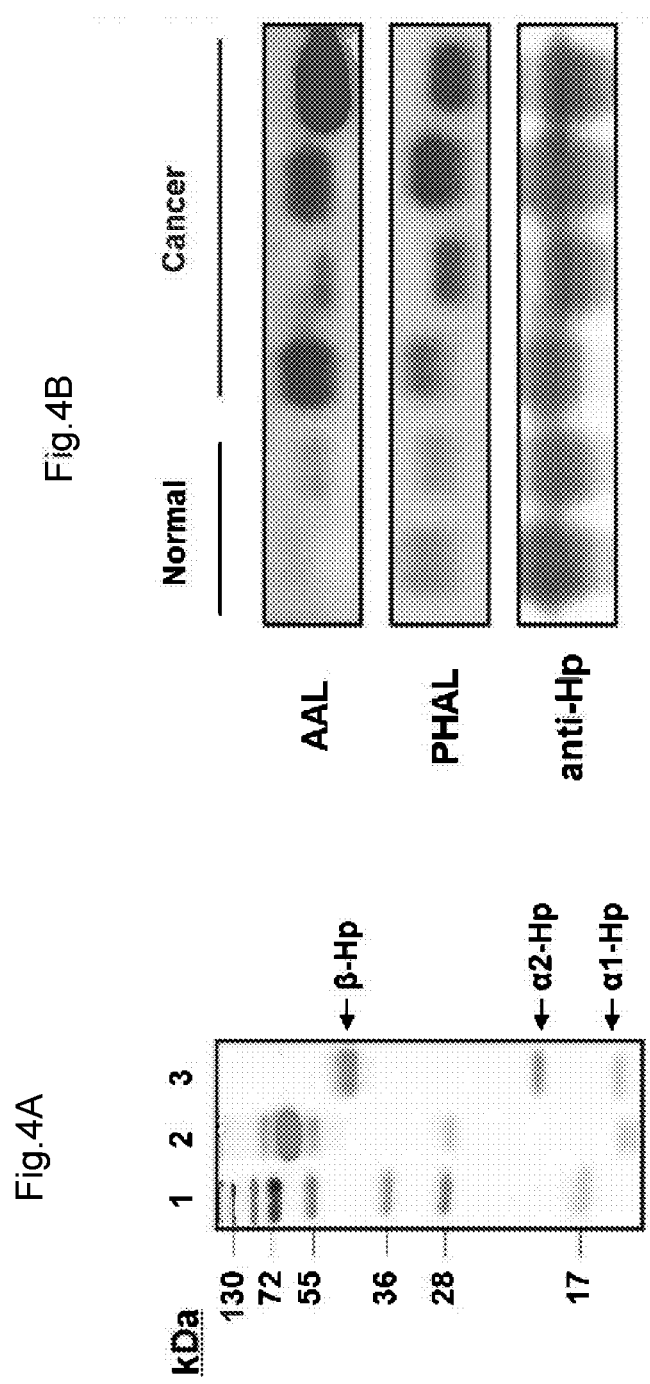
FIGS. 4A and 4B are a purification result of haptoglobins in serum of a normal person and a gastric cancer patient, and a blotting result using AAL lectin, PHA-L lectin, and a haptoglobin antibody, respectively. Line 1 shows a Molecular weight marker; line 2 shows Serum diluted to $\frac{1}{100}$; and line 3 shows haptoglobin purified from the serum of the gastric cancer patient.

In order to confirm a sign obtained by lectin screening, serum-derived haptoglobin is purified using anti-haptoglobin affinity chromatography (FIG. 4A). The reason is that since an accurate glycan structure is hidden by a mixed sample, there is a need to confirm a purified protein. The present inventors confirmed improper glycosylation, that is, fucosylation and the high antennary structure, of haptoglobin of the gastric cancer patient through lectin blotting of the purified haptoglobin. As a result, fucosylation and tri- or higher antennary complex type N-glycan of haptoglobin may be effectively used to diagnose gastric cancer and provide a possibility of gastric cancer diagnosis using AAL lectin and PHA-L lectin having reactivity to the glycan structure.

A fucose residue may be linked to GlcNAc by α-3/4/6 glycosidic linkages, and is associated with Lewis blood group antigens. Multi-antennary N-glycans of haptoglobin are completed by GlcNAcβ1-6Manα1-6Man side branch, identified by PHA-L lectin. There is a need for more research into what fucose residue is enhanced and how an antennary structure is distributed in haptoglobin of a gastric cancer patient. Therefore, the present inventors determined an accurate glycosylation state through integrated glycomics using lectin blotting and chip-based nano-LC/TOF-MS (LC/MS) analysis after immunoaffinity purification. Since in LC-MS, sensitivity is increased and ion fragmentation is decreased as compared to MALDI-MS, the present inventors were able to successfully explain a detailed glycan structure of haptoglobin. As a result, fucosylation and glycosylation modified into a high antennary structure were detected in gastric cancer patient derived haptoglobin.

Figure 2:
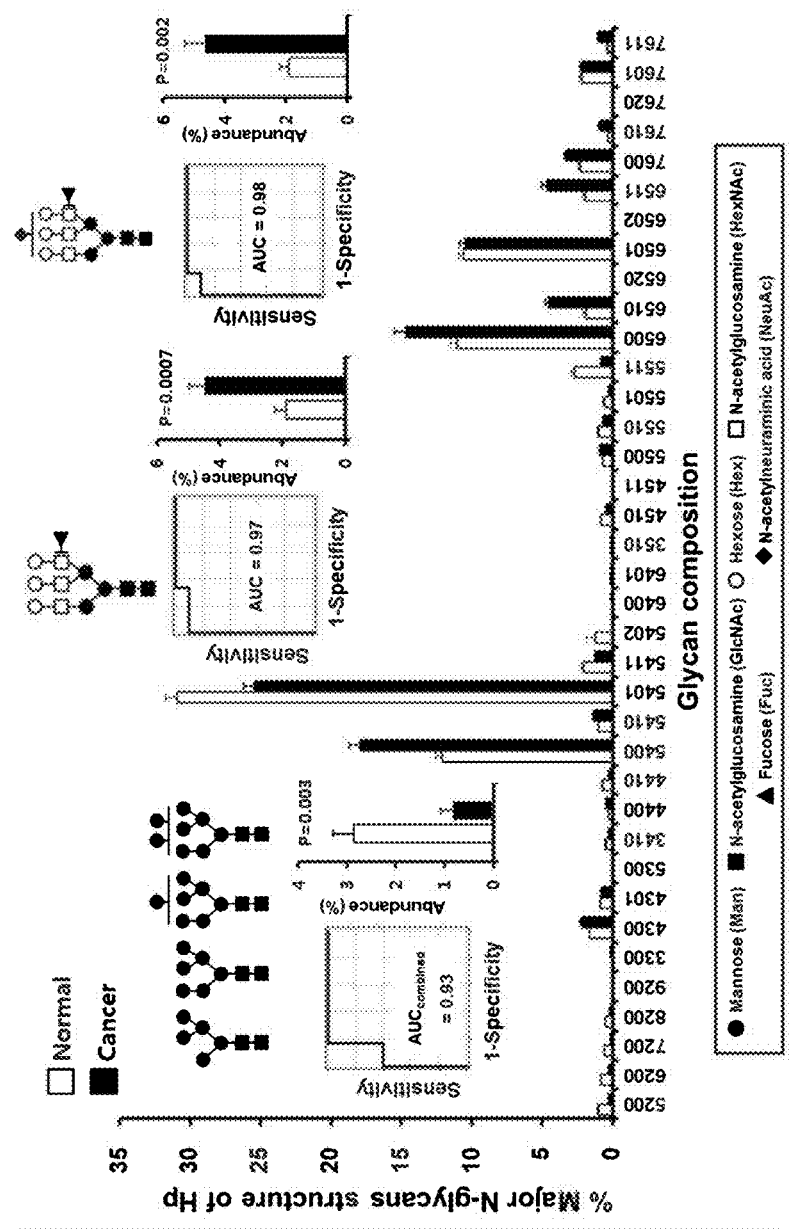
FIG. 2 illustrates N-glycan profiling results of haptoglobins purified from serum of a normal person and a gastric cancer patient. After separating only N-glycans by treating the purified haptoglobins with PNGase F, the N-glycans of the haptoglobins derived from the normal control group and the gastric cancer patient group were confirmed using chip-based nano-liquid chromatography (LC)/time of flight (TOF)-mass spectrometry (MS) (LC/MS). A black circle indicates mannose, a white circle indicates galactose, a square indicates N-acetylhexosamine, a diamond indicates sialic acid, and a triangle indicates fucose.

Several glycan structures having significant differences between the normal control group and the gastric cancer patient group in addition to modified fucosylation and antennary structure may be found through glycan structure profiling. Among tri-antennary structures, there was the biggest difference in a relative value of Hex6-HexNAc5-Fuc1 indicating a mass value of 2151.774 (P value=0.000699), and in various N-glycan structures having a high mannose structure, there were significant differences in relative amounts between the control group and the gastric cancer patient (FIG. 2 and Table 2).

Figure 3A:
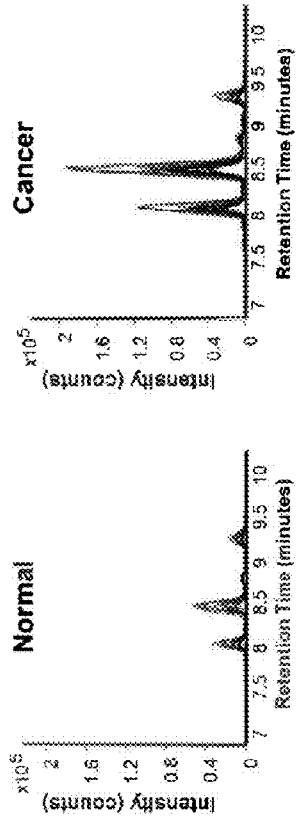
FIGS. 3A and 3B are results illustrating positions of fucose of tri-antennary glycans in haptoglobins separated from the serum of a normal person and a gastric cancer patient.
Figure 3B:
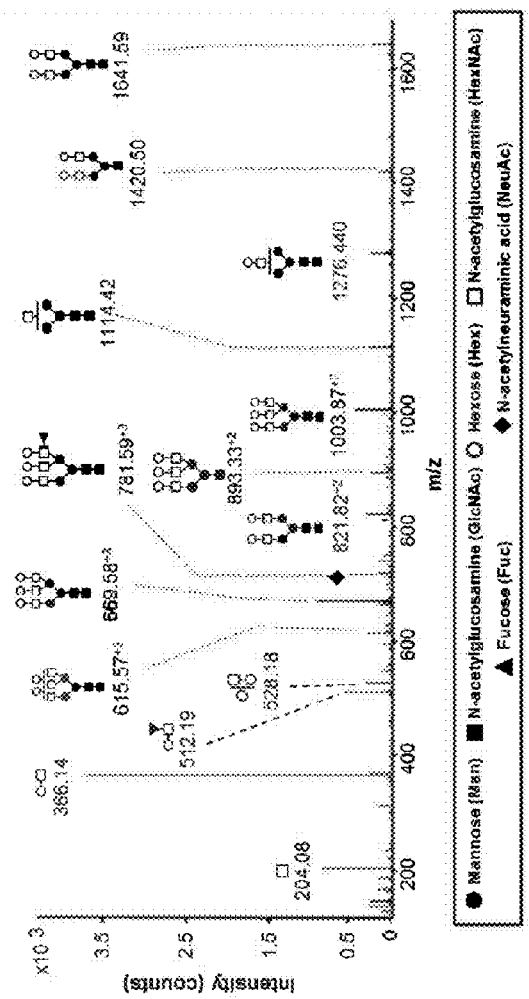

The present inventors directly found improper glycosylation of fucose in serum-derived haptoglobin of the gastric cancer patient. In some study results, since it was reported that core fucose was not transferred to antennae, but fucose redistribution occurred between outer arm (antennae) fucoses or core fucosylation occurred in a certain disease, there was a need to confirm a position of fucose in a glycan form of the gastric cancer patient-derived haptoglobin. A fucosylated structure including the outer arm fucose to have tri-antennary and tetra-antennary complex type N-glycans depending on linkage of monosaccharide may become a Lewis antibody. Interestingly, the present inventors found that the outer arm fucose (such as Hex1-HexNAc1-Fuc1 glycan fragments, m/z 512.19) was present in gastric cancer patient-derived haptoglobin, but did not confirm the presence of core fucosylation (such as HexNAc-Fuc or HexNAc2-Fuc glycan fragments) (FIG. 3B).

The present inventors detected that the tri-antennary and tetra-antennary complex type N-glycans were relatively increased. Most of the glycan structures were compared between the normal control group and the gastric cancer patient group through haptoglobin glycan structure profiling, several N-glycan structures having significantly differences therebetween were summarized, and significance thereof was confirmed by p-values (FIG. 2 and Table 2). Further, a difference in high mannose structure between the normal control group and the gastric cancer patient group was found. Interestingly, the difference in the high mannose structure was observed by the chip-based nano-LC/TOF-MS (LC/MS) rather than lectin analysis. The reason is that the glycan structures may be classified with high sensitivity by using this method. This proves that high-sensitive mass spectrometry may be usefully utilized in cancer diagnosis using a biomarker. Therefore, it may be appreciated that improper glycan structures obtained by the result as described above have a potential as a diagnosis marker for early stage gastric cancer as well as all-stage gastric cancer, and these glycans are useful glycan markers capable of replacing current non-specific gastric cancer markers. In addition, the glycan structure of haptoglobin and reactivity thereof to lectin may be easily applied to a lectin-based diagnosis technology for gastric cancer.

The present invention relates to a method for analyzing a gastric cancer biomarker, the method including:

a) separating and purifying haptoglobin from a subject-derived sample;

b) separating a N-glycan from the purified haptoglobin;

c) performing mass spectrometry on a glycan structure of the separated N-glycan; and d) performing quantitative profiling on a mass spectrometry result.

Further, the present invention relates to the method for analyzing a gastric cancer biomarker, wherein the mass spectrometry in step c) is performed on one or more N-glycan structures selected from Hex5-HexNAc2 glycan (1234.4 m/z),
Hex6-HexNAc2 glycan (1396.5 m/z),
Hex7-HexNAc2 glycan (1558.5 m/z),
Hex8-HexNAc2 glycan (1720.6 m/z),
Hex3-HexNAc3 glycan (1113.4 m/z),
Hex4-HexNAc3 glycan (1275.5 m/z),
Hex4-HexNAc4-Fuc1 glycan (1624.6 m/z),
Hex5-HexNAc4 glycan (1640.6 m/z),
Hex5-HexNAc4-Fuc1 glycan (1786.6 m/z),
Hex5-HexNAc4-NeuAc1 glycan (1931.7 m/z),
Hex5-HexNAc4-Fuc1-NeuAc1 glycan (2077.7 m/z),
Hex4-HexNAc5-Fuc1 glycan (1827.6 m/z),
Hex5-HexNAc5-Fuc1 glycan (1989.7 m/z),
Hex5-HexNAc5-NeuAc1 glycan (2134.8 m/z),
Hex6-HexNAc5-Fuc1 glycan (2151.8 m/z),
Hex5-HexNAc5-Fuc1-NeuAc1 glycan (2280.8 m/z),
Hex6-HexNAc5-Fuc1-NeuAc1 glycan (2442.9 m/z),
Hex7-HexNAc6-Fuc1 glycan (2516.9 m/z),
Hex7-HexNAc6 glycan (2370.8 m/z), and
Hex7-HexNAc6-Fuc1-NeuAc1 glycan (2808.0 m/z) structures.

Further, the present invention relates to the method for analyzing a gastric cancer biomarker, wherein the mass spectrometry in step c) is chip-based nano-LC/TOT-MS (LC/MS).

In addition, the present invention relates to the method for analyzing a gastric cancer biomarker, wherein the quantitative profiling in step d) is performed by one or more selected from T-test p-value analysis, receiver-operating characteristic (ROC) curve analysis, and area under the ROC curve (AUC) analysis.

Further, the present invention relates to the method for analyzing a gastric cancer biomarker, wherein at the time of performing the quantitative profiling in step d), a high mannose structure or N-glycosylated antennary variable is added.

In addition, the present invention relates to the method for analyzing a gastric cancer biomarker, wherein the sample in step a) is any one selected from the group consisting of blood, serum, plasma, cells, and a cell culture medium.

Further, the present invention relates to the method for analyzing a gastric cancer biomarker, wherein the quantitative profiling in step d) is performed using one or more selected from T-test p-value analysis, receiver-operating characteristic (ROC) curve analysis, and area under the ROC curve (AUC) analysis on an average value of relative abundances or a sum of quantifies of the high mannose structures in a Hex5-HexNAc2 glycan (1234.4 m/z),
Hex6-HexNAc2 glycan (1396.5 m/z),
Hex7-HexNAc2 glycan (1558.5 m/z), or
Hex8-HexNAc2 glycan (1720.6 m/z) structure. As a result of observing an average value of the entire N-glycan structures of haptoglobin, in 90% of the cancer patients, each of the four high mannose structures accounted for 0.5% or less of relative abundance, and in 16% of the normal patients, each of the four high mannose structures accounted for 0.5% or less of relative abundance, (data were not illustrated).

Further, the present invention relates to the method for analyzing a gastric cancer biomarker, wherein the quantitative profiling in step d) is performed by one or more selected from T-test p-value analysis, receiver-operating characteristic (ROC) curve analysis, and area under the ROC curve (AUC) analysis on one or more selected from Hex6-HexNAc5-Fuc1 glycan (2151.8 m/z) and
Hex7-HexNAc6-Fuc1 glycan (2516.9 m/z) structures, or an average value or a sum of quantities of two glycan structures.

In addition, the present invention relates to the method for analyzing a gastric cancer biomarker, further comprising, after step c), determining a subject as an individual with gastric cancer or a risk of gastric cancer in a case of selecting one or more from Hex4-HexNAc5-Fuc1 glycan (1827.6 m/z),
Hex5-HexNAc5-Fuc1 glycan (1989.7 m/z),
Hex6-HexNAc5-Fuc1 glycan (2151.8 m/z), Hex5-HexNAc5-Fuc1-NeuAc1 glycan (2280.8 m/z),
Hex6-HexNAc5-Fuc1-NeuAc1 glycan (2442.9 m/z),
Hex7-HexNAc6-Fuc1 glycan (2516.9 m/z), and
Hex7-HexNAc6-Fuc1-NeuAc1 glycan (2808.0 m/z) structures and additionally performing extracted compound chromatograms (ECC) and collision induced dissociation (CID) MS/MS to confirm a glycan structure of fucose positioned at the antennae.

Further, the present invention relates to a kit for gastric cancer diagnosis, the kit including an anti-haptoglobin antibody and one or more lectins of *Aleuria aurantia* agglutinin (AAL) lectin and *Phaseolus vulgaris*-L agglutinin (PHA-L) lectin.

Further, the present invention relates to the kit for gastric cancer diagnosis, wherein the AAL lectin or the PHA-L lectin is bound to a ligand.

In addition, the present invention relates to the kit for gastric cancer diagnosis, wherein the ligand is biotin, avidin, or streptavidin.

Further, the present invention relates to the kit for gastric cancer diagnosis, further including a ligand-specific binding molecule bound to a chromogenic enzyme or fluorescent molecule.

In addition, the present invention relates to the kit for gastric cancer diagnosis, wherein the chromogenic enzyme is horseradish peroxidase (HRP) or alkaline phosphatase.

Further, the present invention relates to the kit for gastric cancer diagnosis, wherein the fluorescent molecule is any one selected from the group consisting of colloid gold, poly L-lysine-fluorescein isothiocyanate (poly L-lysine-FITC), and rhodamine-B-isothiocyanate (RITC).

In the kit for gastric cancer diagnosis according to the present invention, it is preferable to use AAL lectin or PHA-L lectin bound to biotin or a ligand, which is a biotin derivative having substantially the same binding affinity as that of biotin to avidin or streptavidin, and it is preferable to use the ligand to which a visualized conjugate is bound, wherein the chromogenic enzyme or the fluorescent molecule bound to the ligand-specific binding molecule binds to the visualized conjugate. However, the present invention is not limited thereto.

It is preferable that the chromogenic enzyme is horseradish peroxidase (HRP) or alkaline phosphatase, and the fluorescent molecule is any one selected from the group consisting of colloid gold, poly L-lysine-fluorescein isothiocyanate (poly L-lysine-FITC), and rhodamine-B-isothiocyanate (RITC), but the present invention is not limited thereto.

In the kit for gastric cancer diagnosis according to the present invention, a nitrocellulose membrane, a polyvinylidene fluoride (PVDF) film, a well plate synthesized using a polyvinyl resin or a polystyrene resin, a slide glass made of glass, or the like, may be used as a supporter.

In addition, the present invention provides an immunochromatographic strip for gastric cancer diagnosis, the immunochromatographic strip including:
a) an adhesive supporter;
b) a sample pad attached to an upper surface of the adhesive supporter and receiving a test sample to be analyzed;
c) an AAL lectin conjugate pad linked to the sample pad and containing chromogen-binding AAL lectin or a PHA-L lectin conjugate pad linked to the sample pad and containing chromogen-binding PHA-L lectin.
d) a signal detection pad linked to the AAL lectin conjugate pad or the PHA-L lectin conjugate, the signal detection pad including: a test line that is connected to the sample pad and to which an anti-haptoglobin antibody is linearly fixed, and
an AAL lectin control line that is positioned downstream of the test line and to which an anti-AAL lectin antibody or a glycoprotein binding to the AAL lectin is linearly fixed, or
a PHA-L lectin control line that is positioned downstream of the test line and to which an anti-PHA-L lectin antibody or a glycoprotein binding to the PHA-L lectin is linearly fixed; and
e) an absorption pad absorbing the test sample after termination of a signal detection reaction, and positioned downstream of the signal detection pad.

Further, the present invention relates to the immunochromatographic strip, wherein the chromogen is colloidal gold particles.

In addition, the present invention relates to the immunochromatographic strip, wherein the signal detection pad is made of any one selected from the group consisting of nitrocellulose, cellulose, polyethylene, polyether sulfone, and nylon.

Further, the present invention relates to the immunochromatographic strip, wherein the absorption pad includes a porous supporter, and an absorbent dispersed in pores of the porous supporter or adsorbed in or coated on fibers of the porous supporter.

Further, the present invention relates to the immunochromatographic strip, wherein when a colored line is shown in the control line and the test line on the immunochromatographic strip, the test sample is determined as a positive sample for gastric cancer.

In the immunochromatographic strip according to the present invention, first, blood, or the like, which is the test sample, is supplied to the immunochromatographic strip through the sample pad. The sample pad may additionally have a filtering function in order to further improve selectivity for an analyte or minimize an influence of an interference material capable of being contained in the test sample. If necessary, an auxiliary pad containing a material capable of increasing a reaction between the analyte and a conjugate or removing the influence of the interference material may be additionally provided upstream of the sample pad. The blood introduced through the sample pad may move to the conjugate pad positioned upstream of the sample pad by chromatographic movement. The conjugate pad contains an anti-beta-haptoglobin antibody conjugate or anti-haptoglobin antibody conjugate, which specifically binds to beta-haptoglobin or haptoglobin contained in the blood. The conjugate is labeled by gold particles, latex particles, a fluorescent material, an enzyme, or the like. The test sample passed through the conjugate pad moves to the signal detection pad. The signal detection pad may include the test line for detecting whether or not the analyte is present in the test sample and the control line for confirming whether or not the analysis kit is normally operating regardless of the presence or absence of the analyte. To this end, it is preferable that a material (or a signal detection material) selectively and specifically binding to a binding product between the analyte and the conjugate contained in the conjugate pad is coated on the test line, and a material specifically binding to the conjugate contained in the conjugate pad is coated on the control line. The signal detection pad may be formed of a porous membrane pad, and made of nitrocellulose, cellulose, polyethylene, polyether sulfone, nylon, or the like.

In addition, the present invention relates to the immunochromatographic strip, wherein the test sample is any one selected from the group consisting of blood, serum, plasma, cells, and a cell culture medium.

In addition, the present invention relates to a method for analyzing a gastric cancer biomarker, the method including:

a) treating a solid substrate to which an anti-beta-haptoglobin antibody or anti-haptoglobin antibody is attached with a subject-derived sample and washing the substrate;

b) treating the substrate with *Aleuria aurantia* agglutinin lectin (AAL lectin) or *Phaseolus vulgaris*-L agglutinin lectin (PHA-L lectin) and washing the substrate; and c) determining a subject having a significant difference in a degree of binding of the AAL lectin or the PHA-L lectin from a normal person as an individual with gastric cancer or a risk of gastric cancer.

Further, the present invention relates to the method for analyzing a gastric cancer biomarker, wherein the solid substrate in step a) is any one selected from the group consisting of a nitrocellulose (NC) membrane, a polyvinylidene fluoride (PVDF) membrane, a microplate, a glass substrate, a polystyrene substrate, a silicon substrate, and a metal plate.

Further, the present invention relates to the method for analyzing a gastric cancer biomarker, wherein the AAL lectin or the PHA-L lectin in step b) is bound to a ligand.

In addition, the present invention relates to the method for analyzing a gastric cancer biomarker, wherein the ligand is biotin, avidin, or streptavidin.

In addition, the present invention relates to the method for analyzing a gastric cancer biomarker, wherein in step b), after attaching the AAL lectin or PHA-L lectin to which the ligand is bound, a chromogenic enzyme or fluorescent molecule to which a binding molecule specifically binding the ligand is attached is bound thereto.

In addition, the present invention relates to the method for analyzing a gastric cancer biomarker, wherein the chromogenic enzyme is horseradish peroxidase (HRP) or alkaline phosphatase.

Further, the present invention relates to the method for analyzing a gastric cancer biomarker, wherein the fluorescent molecule is any one selected from the group consisting of colloid gold, poly L-lysine-fluorescein isothiocyanate (poly L-lysine-FITC), and rhodamine-B-isothiocyanate (RITC).

In addition, the present invention relates to the method for analyzing a gastric cancer biomarker, wherein the degree of binding in step c) is measured by any one method selected from the group consisting of a western blotting method, an enzyme-linked immunosorbent assay (ELISA) method, an immunoprecipitation method, and an immunofluorescence method.

In addition, the present invention relates to the method for analyzing a gastric cancer biomarker, wherein the subject-derived sample is any one selected from the group consisting of blood, serum, plasma, cells, and a cell culture medium.

The present invention provides a method for gastric cancer diagnosis based on the AAL lectin or PHAL lectin having reactivity to the glycan structure by observing that in fucosylatin or 1-6 GlcNAc branching in haptoglobin derived from serum of the gastric cancer patient group was remarkably increased as compared to the normal control group.

In addition, the present invention provides a method capable of confirming a plurality of high-sensitivity and high-specificity glycan structures, of which abundances are remarkably different in haptoglobin derived from the gastric cancer patient group as compared to the normal control group, at once through mass spectrometry of glycans according to the present invention, and capable of diagnosing gastric cancer using the glycan structures unlike a method according to the related art for analyzing only an amount of a specific protein.

Hereinafter, a configuration of the present invention will be described in more detail through the following Examples. However, those skilled in the art will appreciate that the scope of the present invention is not limited to the Examples.

Raw Materials and Other Reagents

Biotinylated *Aleuria aurantia* (AAL) lectin (binding to Fuca1-3/4/6GlcNAc), biotinylated *Phaseolus vulgaris*-E (PHA-E) lectin (binding to bisected complex type glycans), biotinylated *Phaseolus vulgaris*-L (PHA-L) lectin (binding to tri-antennary and tetra-antennary complex type glycans), biotinylated wheat germ agglutinin (WGA: binding to terminal N-acetylglucosamine or sialic acid), and biotinylated concanavaline A (Con A: binding to oligomannose type glycan) were obtained from Vector Laboratories (Burlingame, Calif.). Commercialized human haptoglobin and ExtrAvidin Peroxidase were purchased from Sigma (St. Louis, Mo.). Rabbit anti-human beta-haptoglobin antibody was purchased from Dako (Carpinteria, Calif.). Goat anti-rabbit IgG horseradish peroxidase (HRP) was purchased from Santa Cruz Biotechnology (Santa Cruz, Calif.) was used. Peptide N-glycosidase F (PNGase) was purchased from New England Biolabs (MA, USA). Graphitized carbon cartridges manufactured by Grace Davison Discovery Sciences (IL, USA) were used. ESI-TOF Calibrant Mix G1969-85000 manufactured by Agilent Technologies (CA, USA) was used. All the reagents were of analytical grade or better.

Serum Samples of Gastric Cancer Patient and Normal Person

Serum samples were obtained from Chungnam National University Hospital, a member of National Biobank of Korea. Clinical information of 10 gastric cancer patients and 6 normal persons was summarized in Table 1. The patients were subjected to biopsy and diagnosed by pathologists. This study was approved by Ethics Commission of Korea Advanced Institute of Science and Technology (KAIST), and after receiving informed consent from the normal persons and the gastric cancer patients participating in this study, this study was conducted.

Purification of Haptoglobin from Human Serum

An anti-haptoglobin affinity column was manufactured using the anti-haptoglobin antibody, and purification was performed. 500 µl of serum was obtained from each of the 10 gastric cancer patients and the 6 normal persons, diluted in a 4 ml of phosphate-buffered saline (PBS, 10 mM phosphate buffer/2.7 mM KCl/137 mM NaCl, pH 7.4), applied to the anti-haptoglobin affinity column, and incubated on a rotary stirrer at room temperature for 2 hours. The column was washed with 30 ml of PBS to remove unbound materials, and haptoglobin was eluted with elution buffer (0.1 M glycine/0.5 M NaCl, pH 2.8) and then fractionated in a tube containing neutralization buffer (1.0 M Tris-HCl, pH 9.0). After the eluate was concentrated, a surfactant was removed by a centrifugal filter (nominal molecular weight limit (NMWL); 10,000, Amicon Ultra, Millipore). Thereafter, the haptoglobin was analyzed using Quant-iT Assay Kit (Invitrogen, Carlsbad, Calif.), and 12.5% SDS-PAGE and Coomassie blue staining were performed. The sample was freeze-dried and stored at −80° C. until analysis.

β-Haptoglobin Lectin Blotting and Western Blotting

Lectin blotting was performed by slightly modifying a method according to the related art. That is, 0.5 µl of serum and 0.5 mg of haptoglobin was electrophoresed by 10% and 12.5% SDS-PAGE, transferred to a PVDF membrane (Millipore, Billerica, Mass.), and then blotted using each of the biotinylated lectins (AAL, PHA-E, PHA-L, WGA, ConA). The PVDF membrane was blocked with T-TBS [TBS (140 mM NaCl, 10 mM Tris-HCl, pH 8.0)/0.05% Tween 20] containing 5% bovine serum albumin (BSA) at room temperature for 1 hour. After the membrane was washed three times for 5 minutes, the membrane was incubated overnight in a cold room using T-TBS containing the biotinylated lectin diluted to 1:1,000 to 1:5,000. Thereafter, the membrane was washed with T-TBS three times and incubated at room temperature for 1 hour using ExtrAvidin-Peroxidase diluted to 1:3,000. Then, the membrane was washed with T-TBS three times, and developed using an enhanced chemiluminescence (ECL) Supersignal kit (Pierce ECL Western Blotting Substrate, Thermo Science, Rockford, Ill.). In order to prepare the haptoglobin in an amount suitable for being loaded, the same blots after lectin blotting were subjected to reblotting using the anti-haptoglobin antibody. In brief, the membrane was incubated at room temperature for 1 hour in a stripping buffer (Candor Bioscience GmbH, Weissensberg, Germany), washed with T-TBS five times, blocked with 5% BSA for 1 hour, incubated overnight in the cold room using the rabbit anti-haptoglobin antibody diluted to 1/50,000, subjected to immunoblotting, washed with T-TBS three times, incubated for 1 hour using the goat anti-rabbit IgG-HRP diluted to 1/5,000, washed with T-TBS three time, and then, developed using an ECL solution.

In-gel Protein Digestion

Protein bands of interest were excised and digested in-gel using sequencing grade-modified trypsin (Promega, Madison, Wis., USA). In brief, a target protein spot was excised from the gel, placed in a polypropylene (Eppendorf) tube, and then washed five times with 150 it of acetonitril/25 mM ammonium bicarbonate (1:1, pH 7.8). A gel slice was dried using a Speedvac concentrator and then rehydrated using 30 µl of 25 mM ammonium bicarbonate (pH 7.8) containing 20 ng of trypsin. After incubation at 37° C. for 20 hours, the liquid was transferred to a new polypropylene tube. Tryptic peptides remaining in a gel matrix were extracted at 30° C. for 40 minutes with 20 µl of 50% (v/v) aqueous acetonitrile containing 0.1% (v/v) formic acid. A combined supernatant was evaporated in the Speedvac concentrator, and the resultant was dissolved in 8 µl of 5% (v/v) aqueous acetonitrile containing 0.1% (v/v) formic acid to thereby be used for mass spectrometry.

Identification of Proteins Using LC-MS/MS

The prepared tryptic peptides were analyzed using reverse-phase capillary high-performance liquid chromatography (HPLC) coupled with a Finnigan LCQ ion trap mass spectrometer. A 0.1×20 mm trapping column and a 0.075× 130 mm resolving column were both packed with Vydac 218MS low trifluoroacetic acid C18 beads (5 µm diameter, 300 Å pore size; Vydac, Hesperia, Calif., USA). After the tryptic peptides were captured in the trapping column for 10 minutes together with 5% (v/v) aqueous acetonitrile containing 0.1% (v/v) formic acid, the captured peptides were eluted with a 50 minute gradient of 5 to 80% (v/v) aqueous acetonitrile containing 0.1% (v/v) formic acid at a flow rate of 0.2 µl/min. The full mass scan range mode for MS/MS was m/z=450 to 2,000 Da. After determining a charge state of an ion on zoom scans, product ion spectra were acquired in MS/MS mode with a relative collision energy of 55%. Spectra from MS/MS were processed using a TurboSEQUEST software (Thermo Quest, San Jose, Calif.). The generated peak list files were used to obtain either National Center for Biotechnology Information (NCBI) database or Matrix Science database (MSDB) using the MASCOT program (http://www.matrixscience.com).

N-glycan Release by Enzyme

N-glycan release by enzymes was performed by slightly modifying a method according to the related art. In brief, purified serum haptoglobin was denatured by rapid thermal cycling (25 to 100° C.) in an aqueous solution of 100 mM ammonium bicarbonate and 5 mM dithiothreitol. After cooling, 2.0 µl (or 1,000 U) of PNGase F was added thereto, and a mixture was incubated in a water bath at 37° C. for 16 hours.

N-glycan Enrichment with Graphitized Carbon Solid-Phase Extraction

Solid-phase extraction of the N-glycan was performed by slightly modifying an optimization method according to the related art. In brief, graphitized carbon cartridges (150 mg, 4.0 ml, Grace Davison) were washed with an aqueous solution containing 80% acetonitrile/0.1% trifluoroacetic acid (v/v), followed by conditioning using ultra-pure water. Haptoglobin fragments were loaded in the cartridges, and washed with ultra-pure water, thereby removing salts and a buffer. The N-glycans were eluted by sequentially adding an aqueous solution containing 10% acetonitrile, an aqueous solution containing 20% acetonitrile, and an aqueous solution containing 40% acetonitrile/0.05% trifluoroacetic acid (v/v). The sample was vacuum-dried.

Chip-Based Nano-LC/MS (LC/MS) and MS/MS

Nano-liquid chromatography (LC) separation was performed according to the related art. 2.0 µl of a combination of N-glycan fractions of each of the samples was injected into a nano-LC column (Agilent Technologies) on which a chip was placed using an auto-sampler. The nano-LC column was composed of a 9×0.075 mm inner diameter (i.d.) enrichment column and a 43×0.075 mm i.d. analytic column, and both of the columns were packed with porous graphitized carbon (5 µm). A rapid glycan elution gradient was delivered at a rate of 0.3 µL/min using solutions of (A) 3.0% acetonitrile and 0.1% formic acid (v/v) in water, and (B) 90.0% acetonitrile and 0.1% formic acid (v/v) in water, ramping from 6% B solution to 100% B solution for 20 minutes. The remaining non-glycan compounds were flushed out with 100% B solution prior to re-equilibration. After separation using chromatography, the glycans were ionized using a chip-integrated nano-ESI spray tip and analyzed using a Q-TOF mass spectrometer (Model 6530, Agilent Technologies) according to the related art. Calibrant molecules (ESI-TOF Calibrant Mix G1969-85000, Agilent Technologies) were directly injected into an electrospray, thereby making it possible to measure an internal mass. MS spectra were acquired in a positive ionization mode over a mass range of m/z 500 to 2000 with an acquisition time of 1.5 seconds per spectrum. MS/MS spectra were acquired in a positive ionization mode over a mass range of m/z 1000 to 3000 with an acquisition time of 1.5 seconds per spectrum. Following MS scan, precursor compounds were automatically selected for MS/MS analysis by an acquisition software based on ion abundance and charge state (z=2 or 3), separated in a quadrupole with a mass bandpass full width at half maximum (FWHM) of 1.3 m/z, and fragmentized by CID according to the following Equation.

$$V_{collision} = 1.8V \left( \frac{m/z}{100\ Da} \right) - 4.8V$$

Here, $V_{collision}$ indicates a voltage applied across collision cells in order to accelerate a precursor and fragmentate the precursor. Raw LC-MS data were analyzed using a molecular feature extractor algorithm included in MassHunter qualitative analysis software (version B.04.00 SP2, Agilent Technologies). MS peaks were filtered with a signal-to-noise ratio of 5.0, and sequences of the glycans were determined (deconvoluted) by removing sugars one at a time, in order to acquire masses of compounds, ion abundance, and a retention time list.

N-Glycan Identification by Accurate Mass

Masses of compounds detected by MALDI-MS and nano-LC/MS were compared with accurate masses in glycan database of all possible complex, hybrid, and high mannose glycan compositions based on known biosynthetic pathways and glycosylation patterns. Mass for each extracted compound chromatograms (ECC) peak, determined by a glycan sequence determination method was compared with a theoretical mass of a glycan using a mass error tolerance of 20 ppm. Only glycan configurations including hexose, N-acetylhexosamine (HexNAc), fucose, and N-acetylneuraminic acid (NeuAc) were considered as in a human serum-derived sample set. N-glycans extracted from respective samples were comparatively analyzed using T-test p-value analysis, receiver-operating characteristic (ROC) curve analysis, area under the ROC curve (AUC) analysis, and the like.

Result 1: Confirmation of Lectin-Binding Glycoprotein Including Improper Glycan in Serum of Gastric Cancer Patient Compared with Serum of Normal Person In order to confirm a different glycosylation pattern of serum proteins of a gastric cancer patient as compared to a normal person, a lectin blotting method was selected. The reason is that it is possible to purchase a large amount of lectin and it is easy to apply the lectin to analysis of glycans in serum. 0.5 µl of each serum obtained from a total of six subjects composed of healthy persons (control group) and gastric cancer patients (stages I to IV) was electrophoresed in 10% acryloamide gel, stained with Coomassie brilliant blue, and subjected to western blotting using various lectins together with an anti-human haptoglobin antibody. Lines 1 and 2 correspond to the normal control group, and lines 3 to 6 corresponds to stages I to IV of gastric cancer, respectively (FIG. 1A). In order to compare glycosylation patterns of glycoproteins obtained from crude serum of the gastric cancer patients and normal persons, five kinds of lectins, AAL, PHA-L, PHA-E, WGA, and Con A were selected. All proteins bound to the lectins were detected, and as a result, reactivity of the lectins to a single spot located at about 45 kDa was significantly different in the gastric cancer patient group from in the normal control group. The present inventors observed that fucosylation and β1-6 GlcNAc branching were increased in the spot derived from the serum of the gastric cancer patient group. In order to confirm a spot corresponding to a case in which the glycosylation pattern was increased in the gastric cancer patients, bands of lines 1 and 5 were excised and digested in-gel. A tryptic peptide as described above was analyzed using LC-MS/MS. This peptide was identified as haptoglobin (Hp) by a database search. Further, in order to confirm a molecular weight and a content of haptoglobin using the anti-haptoglobin antibody, haptoglobin was subjected to western blotting (FIG. 1A). As a result of testing a blotting index value of glycan epitopes in the haptoglobin, as compared to other glycan structures, there were significant differences in fucose and high antennary structure between the normal person, the early-stage gastric cancer patient, and the late-stage gastric cancer patient (FIG. 1B).

Result 2: Analysis of Gastric Cancer-Specific N-Linked Glycan of Haptoglobin

A detailed glycosylation pattern of haptoglobin was analyzed using a chip-based nano-LC/TOF-MS (LC/MS) system. This system may distinguish heterogeneity of glycans having different linkage or different antennae, and provide higher sensitivity as compared to MALDI-MS and conventional LC/MS. The reason is that this system has additional advantages in that low energy ions, a wide dynamic range, and unmatched retention time reproducibility may be provided. The present inventors analyzed N-glycans of haptoglobins derived from serum samples (n=16) of normal persons and patients two times (FIG. 2 and Table 2). After separating only the N-glycans of the haptoglobins by PNGase F treatment, the N-glycans of the haptoglobins derived from a normal control group and a gastric cancer patient group were compared using chip-based nano-LC/TOF (LC/MS). All structures within upper 95% of the entire glycan structures confirmed in respective samples were used, and quantified values were compared. Among the corresponding N-glycan structures, high mannose structures, Hex6-HexNAc5-Fuc1, a glycan structure 6510, having a mass of 2151.774 among tri-antennary structures, Hex7-HexNAc5-Fuc1, a glycan structure 7610, having a mass of 2442.876 among tetra-antennary structures, and the like, had AUC values of 0.90 or more. In the case of a sum of the high mannose structures, at a cutoff value of 0.8985, sensitivity was 60% and specificity was 100%. Further, in the cases of the glycan structures 6510 and 7610, at cutoff values of 3.014 and 2.616, sensitivity was 90% and specificity was 100%, respectively. High-sensitive and high-specificity N-glycan structures of haptoglobin, showing significant differences (p<0.05) between the serum from the normal person and the gastric cancer patient, and having high AUC values of 0.8 or more were summarized in Table 2.

Result 3: Determination of Different Fucose Position of Haptoglobin by Nano LC-MS/MS In order to determine a position of fucose in tri- or higher antennary glycan structures of haptoglobin derived from the serum of the gastric cancer patient, the present inventors extract compound chromatograms, and performed CID MS/MS targeting a specific glycan structure (Hex6-HexNAc5-Fuc1, 2151.774 m/z). As illustrated in Table 2, in the tri-antennary and tetra-antennary glycan types, Hex6-HexNAc5-Fuc1 and Hex7-HexNAc6-Fuc1 were structures showing significant differences between the normal person and the gastric cancer patient, respectively. FIG. 3A illustrates overlaid raw extracted compound chromatograms (ECC) for complex-fucosylated tri-antennary N-glycan composition, Hex6-HexNAc5-Fuc1. The present inventors were able to separate a glycan isomer having a target structure, and a total of four isomers (retention time: 8.03, 8.45, 8.83, and 9.26 minutes) were observed in the serum of the normal control group and the gastric cancer patient group. An entire intensity of the isomers was higher in the gastric cancer patient group than in the normal group. In addition, the present inventors observed an outer arm (antenna) fucose in CID fragmentation of haptoglobin N-glycans, but did not observe fragment ions associated with core fucosylation (FIG. 3B). A fragment ion at m/z 512.19 (Hex1-HexNAc1-Fuc1) corresponded to antennary fucosylation, and identified as an isomer of a fucosylated tri-antennary N-glycan structure, Hex6-HexNAc5-Fuc1 (triply protonated, m/z 781.59). The present inventor could prove and complete data indicating increases in fucosylation in haptoglobin having a tri-antennary or tetra-antennary N-glycan structure through ECCs and targeted CID MS/MS.

Result 4: Lectin Blotting of Haptoglobin Purified from Normal Person and Gastric Cancer Patient Using AAL Lectin and PHA-L Lectin Since a more accurate structure of glycan may be determined in a purified glycoprotein as compared to a mixed sample, the present inventors performed anti-haptoglobin affinity chromatography using 500 µl of serum, thereby purifying haptoglobin, which is an abundant serum glycoprotein (FIG. 4A). Haptoglobin is composed of two kind of polypeptide chains, that is, alpha and beta chains, and four N-glycosylation sites 184, 207, 211, and 241 are present only in the beta chain. In FIG. 4B, abnormal glycans present in the beta chain of the purified haptoglobin were confirmed using AAL lectin and PHA-L lectin, and the presence or absence of the haptoglobin was confirmed using the haptoglobin antibody. As a result, as illustrated in Table 3, it may be appreciated that in the case of the AAL lectin, in 50% (5/10) of the gastric cancer patients, a blotting index was 0.6 or more, in 60% (6/10) of the gastric cancer patients, the blotting index was 0.4 or more, and in 90% (9/10) of the gastric cancer patients, the blotting index was 0.2 or more, but in 17% (1/6) of the normal persons, the blotting index was 0.6 or more, in 33% (2/6) of the normal persons, the blotting index was 0.4 or more, and in 67% (4/6) of the normal persons, the blotting index was 0.2 or more. It may be appreciated that in the case of the PHA-L lectin, in 80% (8/10) of the gastric cancer patients, a blotting index was 0.6 or more, in 100% (10/10) of the gastric cancer patients, the blotting index was 0.4 or more, and in 1,000% (10/10) of the gastric cancer patients, the blotting index was 0.2 or more, but in 17% (1/6) of the normal persons, the blotting index was 0.6 or more, in 33% (2/6) of the normal persons, the blotting index was 0.4 or more, and in 67% (4/6) of the normal persons, the blotting index was 0.2 or more. An intensity of the AAL lectin in beta-haptoglobin was higher in the gastric cancer patients than in the normal control group. This result indicates that fucosylated glycans were increased in the haptoglobin of the gastric cancer patients as compared to the normal persons. An intensity of the PHA-L lectin was also further increased in the beta-haptoglobin of the gastric cancer patients as compared to the normal control group. Since the PHA-L lectin has abundant β1-6 GlcNAc antennae, the PHA-L may recognize a tri-antennary or tetra-antennary complex-type glycan structure. Blotting using other lectins was also performed, but relevance was low as compared to the AAL lectin and the PHA-L lectin (not illustrated in data). This result suggests a possibility of lectin-based gastric cancer diagnosis using the AAL lectin or PHA-L lectin and the haptoglobin.

TABLE 1

| Case# | Classification | Sex | Age | Type | TNM stage |
|---|---|---|---|---|---|
| 1 | Gastric Cancer | Male | 60 | Adenocarcinoma | T1N0M0 |
| 2 | | Female | 40 | Adenocarcinoma | T4N3M0 |
| 3 | | Male | 55 | Adenocarcinoma | T4N2M0 |
| 4 | | Male | 77 | Mucinous carcinoma | T4N2M0 |
| 5 | | Male | 42 | signet ring cell carcinoma | T1N1M0 |
| 6 | | Male | 67 | Adenocarcinoma | T1N0M0 |
| 7 | | Female | 71 | Mucinous carcinoma | T3N1M0 |
| 8 | | Male | 45 | Adenocarcinoma | T3N1M0 |
| 9 | | Male | 64 | Adenocarcinoma | T1N0M0 |
| 10 | | Female | 70 | Adenocarcinoma | T1N0M0 |
| 1 | Non-cancer | Female | 53 | | |
| 2 | | Male | 35 | | |
| 3 | | Female | 49 | | |
| 4 | | Female | 58 | | |
| 5 | | Male | 47 | | |
| 6 | | Male | 58 | | |

TABLE 2

| | Composition | | | | Relative abundance(%) | | P-value | |
|---|---|---|---|---|---|---|---|---|
| Glycan Mass/Da | Hex | HexNAc | Fuc | NeuAc | N | C | (t-Test) | AUC |
| High mannose | | | | | | | | |
| 1234.429 | 5 | 2 | 0 | 0 | 0.99 | 0.25 | 0.006095 | 0.95 |
| 1396.482 | 6 | 2 | 0 | 0 | 0.80 | 0.25 | 0.000894 | 0.95 |
| 1558.536 | 7 | 2 | 0 | 0 | 0.55 | 0.15 | 0.031115 | 0.82 |
| 1720.588 | 8 | 2 | 0 | 0 | 0.53 | 0.17 | 0.001023 | 0.92 |
| Mono. Bi-antennary | | | | | | | | |
| 1113.409 | 3 | 3 | 0 | 0 | 0.00 | 0.15 | 0.017783 | 0.75 |
| 1275.457 | 4 | 3 | 0 | 0 | 1.62 | 2.19 | 0.005914 | 0.88 |
| 1624.597 | 4 | 4 | 1 | 0 | 0.71 | 0.22 | 0.027548 | 0.83 |
| 1640.590 | 5 | 4 | 0 | 0 | 12.16 | 17.89 | 0.005223 | 0.88 |
| 1786.646 | 5 | 4 | 1 | 0 | 0.97 | 1.35 | 0.015104 | 0.83 |
| 1931.688 | 5 | 4 | 0 | 1 | 30.95 | 25.38 | 0.034210 | 0.8 |
| 2077.744 | 5 | 4 | 1 | 1 | 2.04 | 1.20 | 0.020931 | 0.88 |
| Tri-antennary | | | | | | | | |
| 1827.647 | 4 | 5 | 1 | 0 | 0.78 | 0.41 | 0.000805 | 0.93 |
| 1989.728 | 5 | 5 | 1 | 0 | 1.00 | 0.63 | 0.046655 | 0.82 |
| 2134.761 | 5 | 5 | 0 | 1 | 0.58 | 0.26 | 0.023866 | 0.88 |
| 2151.774 | 6 | 6 | 1 | 0 | 1.87 | 4.49 | 0.000699 | 0.97 |
| 2280.825 | 5 | 5 | 1 | 1 | 2.69 | 0.72 | 0.006409 | 0.95 |
| 2442.876 | 6 | 5 | 1 | 1 | 1.91 | 4.65 | 0.002128 | 0.98 |

TABLE 2-continued

| Glycan Mass/Da | Composition | | | | Relative abundance(%) | | P-value (t-Test) | AUC |
|---|---|---|---|---|---|---|---|---|
| | Hex | HexNAc | Fuc | NeuAc | N | C | | |
| Tetra-antennary | | | | | | | | |
| 2516.909 | 7 | 6 | 1 | 0 | 0.33 | 0.89 | 0.002792 | 0.9 |
| 2370.848 | 7 | 6 | 0 | 0 | 2.29 | 3.29 | 0.009903 | 0.9 |
| 2807.999 | 7 | 6 | 1 | 1 | 0.35 | 0.99 | 0.004662 | 0.88 |

TABLE 3

| Classification | Sample | Case No. | Blotting Index (AAL) | | | | Blotting Index (PHAL) | | | |
|---|---|---|---|---|---|---|---|---|---|---|
| | | | <0.2 | 0.2-0.4 | 0.4-0.6 | >0.6 | <0.2 | 0.2-0.4 | 0.4-0.6 | >0.6 |
| Normal | | N1 | + | | | | + | | | |
| | | N2 | + | | | | + | | | |
| | | N3 | | | | + | | | | + |
| | | N4 | | | + | | | | + | |
| | | N5 | | + | | | | + | | |
| | | N6 | | | + | | + | | | |
| Gastric cancer | Stage I | GC1 | | | | + | | | + | |
| | Stage I | GC5 | | + | | | | | | + |
| | Stage I | GC6 | | + | | | | | | + |
| | Stage I | GC9 | | | | + | | | | + |
| | Stage I | GC10 | | | | + | | | + | |
| | Stage III | GC7 | + | | | | | | | + |
| | Stage III | GC8 | | + | | | | | | + |
| | Stage IV | GC2 | | | + | | | | | + |
| | Stage IV | GC3 | | | | + | | | | + |
| | Stage IV | GC4 | | | | + | | | | + |
| Positive cases for Normal | | | | | | >0.6, 1/6, 17% | | | | >0.6, 1/6, 17% |
| | | | | | | >0.4, 3/6, 50% | | | | >0.4, 2/6, 33% |
| | | | | | | >0.2, 4/6, 67% | | | | >0.2, 4/6, 67% |
| Positive cases for Cancer | | | | | | >0.6, 5/10, 50% | | | | >0.6, 8/10, 80% |
| | | | | | | >0.4, 6/10, 60% | | | | >0.4, 10/10, 100% |
| | | | | | | >0.2, 9/10, 90% | | | | >0.2, 10/10, 100% |
| Early-stage Cancer (Stage I) | | | | | | >0.6, 3/5, 60% | | | | >0.6, 3/5, 60% |
| | | | | | | >0.4, 3/5, 60% | | | | >0.4, 5/5, 100% |
| | | | | | | >0.2, 5/5, 100% | | | | >0.2, 5/5, 100% |
| Middle- or Late-stage Cancer (Stage III, IV) | | | | | | >0.6, 2/5, 40% | | | | >0.6, 5/5, 100% |
| | | | | | | >0.4, 3/5, 60% | | | | >0.4, 5/5, 100% |
| | | | | | | >0.2, 4/5, 80% | | | | >0.2, 5/5, 100% |

Although the embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention provides a method for gastric cancer diagnosis based on AAL lectin or PHAL lectin having reactivity to a glycan structure by observing that fucosylatin or 1-6 GlcNAc branching in haptoglobin derived from serum of the gastric cancer patient group was remarkably increased as compared to the normal control group.

In addition, the present invention provides a method capable of confirming a plurality of high-sensitivity and high-specificity glycan structures, of which abundances are remarkably different in haptoglobin derived from the gastric cancer patient group as compared to the normal control group, at once through mass spectrometry of glycans according to the present invention, and capable of diagnosing gastric cancer using the glycan structures unlike a method for analyzing only an amount of a specific protein according to the related art.

As described above, the present invention may be useful to rapidly and accurately diagnose gastric cancer.

The present application was performed by "The Development of Basic Technology for Regulating and Controlling Glycan for Preparing Glycan Mutant" (project No. 2013075931), the next-generation applied omics project, supported by the Ministry of Science, ICT, and Future Planning, and managed by the National Research Foundation of Korea, and "The Development of Integrated Bioprocess Technology linked with Animal Cell Incubation-Isolation and Purification-Monitoring technologies" (Project No. 2013K000246), new technology convergence-type growth engine project, supported by the Ministry of Science, ICT, and Future Planning, and managed by Bio-Pharmaceutical Business Center.

The invention claimed is:
1. A method comprising:
separating haptoglobin from a sample derived from a subject;

separating N-glycan by treating the haptoglobin with an enzyme;

performing mass spectrometry on the separated N-glycan; and performing quantitative profiling for a result of the mass spectrometry by one or more selected from the group consisting of a receiver-operation characteristic (ROC) curve analysis, and an area-under-the-ROC curve (AUC) analysis on one or more selected from the group consisting of tri-antennary Hex6-HexNAc5-Fuc1 glycan (2151.8 m/z) and tetra-antennary Hex7-HexNAc6-Fuc1 glycan (2516.9 m/z);

identifying that the subject has gastric cancer or a high risk of gastric cancer when an AUC value of tri-antennary Hex6-HexNAc5-Fuc1 glycan (2151.8 m/z) is 0.9 or higher, when an AUC value of tetra-antennary Hex7-HexNAc6-Fuc1 glycan (2516.9 m/z) is 0.9 or higher, when an average of the AUC value of tri-antennary Hex6-HexNAc5-Fuc1 glycan (2151.8 m/z) and the AUC value of tetra-antennary Hex7-HexNAc6-Fuc1 glycan (2516.9 m/z) is 0.9 or higher, or when a sum of the AUC value of tri-antennary Hex6-HexNAc5-Fuc1 glycan (2151.8 m/z) and the AUC value of tetra-antennary Hex7-HexNAc6-Fuc1 glycan (2516.9 m/z) is 0.9 or higher; and administering a therapeutic drug to said identified subject for treating gastric cancer.

2. The method of claim 1, wherein the mass spectrometry is chip-based nano-liquid chromatography (LC)/time of flight (TOF)-mass spectrometry (MS) (LC/MS).

3. The method of claim 1, wherein the sample is at least one selected from the group consisting of blood, serum, plasma, cells, and a cell culture medium.

4. The method of claim 1, further comprising determining that the subject has gastric cancer or a high risk of gastric cancer if a glycan structure containing fucose positioned at antennae is confirmed by additionally performing extracted compound chromatograms (ECC) and collision induced dissociation (CID) MS/MS on at least one selected from the group consisting of:

Hex4-HexNAc5-Fuc1 glycan (1827.6 m/z),
Hex5-HexNAc5-Fuc1 glycan (1989.7 m/z),
Hex6-HexNAc5-Fuc1 glycan (2151.8 m/z),
Hex5-HexNAc5-Fuc1-NeuAc1 glycan (2280.8 m/z),
Hex6-HexNAc5-Fuc1-NeuAc1 glycan (2442.9 m/z),
Hex7-HexNAc6-Fuc1 glycan (2516.9 m/z), and
Hex7-HexNAc6-Fuc1-NeuAc1 glycan (2808.0 m/z) structures.

* * * * *